(12) United States Patent
Harvey et al.

(10) Patent No.: US 7,267,956 B2
(45) Date of Patent: Sep. 11, 2007

(54) NUCLEIC ACID SEQUENCES FOR DETECTING GENETIC MARKERS FOR CANCER IN A BIOLOGICAL SAMPLE

(75) Inventors: Richard C. Harvey, Thousand Oaks, CA (US); Thomas J. Clark, Jr., San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 380 days.

(21) Appl. No.: 10/978,145

(22) Filed: Oct. 28, 2004

(65) Prior Publication Data

US 2005/0118630 A1 Jun. 2, 2005

Related U.S. Application Data

(62) Division of application No. 10/273,707, filed on Oct. 17, 2002, now Pat. No. 6,811,985, which is a division of application No. 09/493,491, filed on Jan. 28, 2000, now Pat. No. 6,551,778.

(60) Provisional application No. 60/117,640, filed on Jan. 28, 1999.

(51) Int. Cl.
C12Q 1/68 (2006.01)
C07H 21/04 (2006.01)

(52) U.S. Cl. ............... 435/6; 536/23.1; 536/24.32; 536/34.33

(58) Field of Classification Search ............... 536/23.1, 536/24.33, 24.32; 435/6
See application file for complete search history.

(56) References Cited

U.S. PATENT DOCUMENTS

| | | | |
|---|---|---|---|
| 5,283,174 A | 2/1994 | Arnold, Jr. et al. | |
| 5,399,491 A | 3/1995 | Kacian et al. | |
| 5,516,639 A | 5/1996 | Tindall et al. | |
| 5,538,866 A | 7/1996 | Israeli et al. | |
| 5,554,516 A | 9/1996 | Kacian et al. | |
| 5,672,480 A | 9/1997 | Dowell et al. | |
| 5,674,682 A | 10/1997 | Croce et al. | |
| 5,688,649 A | 11/1997 | Croce et al. | |
| 5,698,402 A | 12/1997 | Luderer et al. | |
| 5,710,007 A | 1/1998 | Luderer et al. | |
| 5,766,888 A | 6/1998 | Sobol et al. | |
| 5,773,292 A | 6/1998 | Bander | |
| 5,786,148 A | 7/1998 | Bandman et al. | |
| 5,817,798 A | 10/1998 | Gundling | |
| 5,840,494 A | 11/1998 | Katz et al. | |
| 5,858,673 A | 1/1999 | Price et al. | |
| 5,891,681 A | 4/1999 | Mallet et al. | |
| 5,962,237 A | 10/1999 | Ts'o et al. | |
| 5,976,794 A | 11/1999 | Katz et al. | |
| 6,013,471 A | 1/2000 | Tindall et al. | |
| 6,090,559 A | 7/2000 | Russell et al. | |
| 6,093,796 A | 7/2000 | Tindall et al. | |
| 6,103,237 A | 8/2000 | Saedi et al. | |
| 6,235,486 B1 | 5/2001 | Young et al. | |
| 6,303,361 B1 | 10/2001 | Vihko | |
| 6,479,263 B1 | 11/2002 | Slawin et al. | |
| 6,620,922 B1 | 9/2003 | Xu et al. | |
| 6,630,305 B1 | 10/2003 | Xu et al. | |
| 6,759,515 B1 | 7/2004 | Xu et al. | |

FOREIGN PATENT DOCUMENTS

| | | |
|---|---|---|
| EP | 0843006 A2 | 5/1998 |
| JP | 2000/069969 A | 3/2000 |
| WO | WO96/21042 A2 | 7/1996 |
| WO | WO96/21671 A1 | 7/1996 |
| WO | WO96/26272 A1 | 8/1996 |
| WO | WO97/07242 A1 | 2/1997 |
| WO | WO97/39139 A1 | 10/1997 |
| WO | WO98/02449 A1 | 1/1998 |
| WO | WO98/21365 A2 | 5/1998 |
| WO | WO98/35031 A1 | 8/1998 |
| WO | WO98/40513 A1 | 9/1998 |
| WO | WO98/46788 A2 | 10/1998 |
| WO | WO98/49323 A1 | 11/1998 |
| WO | WO 00/53776 A2 | 9/2000 |
| WO | WO 00/65067 A2 | 11/2000 |
| WO | WO 00/71711 A2 | 11/2000 |
| WO | WO01/76622 A2 | 10/2001 |
| WO | WO01/77317 A1 | 10/2001 |
| WO | WO01/83817 A1 | 11/2001 |
| WO | WO02/103053 A1 | 12/2002 |
| WO | WO03/076610 A2 | 9/2003 |
| WO | WO2004/070056 A2 | 8/2004 |

OTHER PUBLICATIONS

Black et al., "Expression of a prostate-associated protein, human glandular kallikrein (hK2), in breast tumours and in normal breast secretions", Br J Cancer, (2000), 82(2):361-367 (Abstract).

Daher et al., "Prostate-specific antigen and new related markers for prostate cancer", Clin Chem Lab Med, (1998), 36(9):671-681 (Abstract XP-002147837).

Darson et al., "Human Glandular Kallikrein 2 Expression in Prostate Adenocarcinoma and Lymph Node Matastases", Urology, (1999), 53(5):939-944.

Deguchi et al., "Detection of Micrometastatic Prostate Cancer Cells in Lymph Nodes by Reverse Transcriptase-Polymerase Chain Reaction", Cancer Res, (1993), 53:5350-5354.

(Continued)

Primary Examiner—Gary Benzion
Assistant Examiner—Cynthia Wilder
(74) Attorney, Agent, or Firm—Christine Gritzmacher; Carlos Fisher

(57) ABSTRACT

Nucleic acid sequences for detecting the presence of nucleic acids, particularly mRNA, encoding human prostate-associated genetic markers encoding prostate-specific antigen (PSA), prostate specific membrane antigen (PSMA) or human kallikrein 2 (hK2) are disclosed. Preferred combinations of nucleic acid sequences amplifying and detecting the prostate-associated genetic markers RNA, used in methods that include amplification of the target sequences and detection of the amplified sequences are disclosed. Methods of detecting the presence of prostate-associated genetic marker nucleic acids, particularly mRNA, in a biological sample of non-prostate origin are disclosed.

17 Claims, 5 Drawing Sheets

OTHER PUBLICATIONS

Diamandis et al., "Prostate Cancer, Prostate-Specific Antigen, and the Polymerase Chain Reaction", Clin Chem, (1995), 41(2):177-179.
Diamandis et al., "Detection of prostate-specific antigen immunoreactivity in breast tumors", Breast Cancer Res Treat, (1994), 32:301-310.
Diamandis, "Prostate-specific antigen: Its usefulness in clinical medicine", Trends in Endocrinol Metab, (1998), 9(8):310-316 (Abstract XP-002147838).
Katz et al., "Molecular Staging of Prostate Cancer with the Use of Enhanced Reverse Transcriptase-PCR Assay", Urology, (1994), 43(6):765-775.
Lundwall et al., "Molecular cloning of human prostate specific antigen cDNA", FEBS Lett, (1987), 214(2):317-322.
Lundwall et al., Genbank accession No. X05332, submitted Nov. 1989.
Malatesta et al., "Prostate-specific antigen found in type I breast cyst fluids is a secretory product of the apocrine cells lining breast gross cysts", Breast Cancer Res Treat, (1999), 57(2):157-163 (Abstract).
Mattano, Jr. et al, "Sensitive Detection of Rare Circulating Neuroblastoma Cells by Reverse Transcriptase-Polymerase Chain Reaction", Cancer Res, (1992), 52:4701-4705.
Monne et al., "Molecular Characterization of Prostate-Specific Antigen Messenger RNA Expressed in Breast Tumors", Cancer Res, (1994), 54:6344-6347.
Partin et al., Use of Human Glandular Kallikrein 2 for the Detection of Prostate Cancer: Preliminary Analysis, Urology, (1999), 54(5):839-845.
Riegman et al., Genbank accession No. M21897, submitted Jan. 1995.
Romppanen et al., "Measurement of prostate-specific antigen in detection of benign or malignant breast disease in women", Br J Cancer, (1999), 79(9/10):1583-1587.
Vessella et al., "The use of the polymerase chain reaction to detect metastatic prostate cancer cells in lymph nodes and bone marrow", Proc Am Assn Cancer Res, (1992), 33:396, (Abstract No. 2367).
Wu et al., "Detection of micrometastases in breast cancer by the polymerase chain reaction: A feasibility study", US and Canadian Acad Pathol Ann Mtg, 109A, (1990), (Abstract No. 641).
Yu et al., "Prostate-specific antigen (PAS) in women", J La State Med Soc, (1999), 151(4):209-213 (Abstract).
Yu et al., Immunoreactive Prostate-Specific Antigen Levels in Female and Male Breast Tumors and Its Association With Steroid Hormone Receptors and Patient Age, Clin Biochem, (1994), 27(2):75-79.
US 6,512,094, 01/2003, Xu et al. (withdrawn)

NUCLEIC ACID SEQUENCES FOR DETECTING GENETIC MARKERS FOR CANCER IN A BIOLOGICAL SAMPLE

This application is a divisional of U.S. Ser. No. 10/273,707 filed Oct. 17, 2002 now U.S. Pat. No. 6,811,985, which is a divisional of U.S. Ser. No. 09/493,491 filed Jan. 28, 2000, now U.S. Pat. No. 6,551,778, which claims the benefit under 35 U.S.C. § 119(e) of the provisional application of Ser. No. 60/117,640, filed Jan. 28, 1999, all of which are incorporated by reference.

FIELD OF THE INVENTION

This invention relates to detection of nucleic acids that serve as cancer markers in biological samples, and specifically relates to methods for specifically detecting nucleic acids encoding prostate-specific antigen (PSA), prostate-specific membrane antigen (PSMA), and/or human glandular kallikrein (hK2) which, when present individually or together in a biological sample are indicative of the presence of cancer in the organism, particularly prostate and breast cancers.

BACKGROUND OF THE INVENTION

Prostate cancer is a leading cause of death in men, particularly in men over 60 years of age. The biological aggressiveness of the cancer varies greatly between individuals, with some cancers remaining as latent tumors which do not progress to clinical significance, and others rapidly progressing and metastasizing to a fatal disease within a few years. Clinical diagnosis and staging of prostate tumors has relied on digital rectal examination (DRE), computed tomography (CT) scans and/or endorectal magnetic resonance imaging (MRI). In addition, detection of cells bearing molecular markers specific to or highly expressed in prostate tissue has been used diagnostically.

Prostate specific antigen (PSA) is a protease made in high concentrations in prostatic epithelial cells and secreted into ducts of the prostate gland. PSA is a molecular marker for detection of prostate cancer (prostatic adenocarcinoma). Prostatic acid phosphatase (PAP) is another secreted enzyme that has been used as a serum marker for detection of prostatic metastases. A prostate-specific membrane antigen (PSMA), which is also highly expressed in prostate cancer tissues including bone and lymph node metastases, has been characterized, isolated and the gene encoding it has been cloned (U.S. Pat. No. 5,538,866 to Israeli et al.; O'Keefe D. S. et al, 1998, Biochim. Biophys. Acta 1443(1-2):113-127). Human glandular kallikrein-2 (hK2) is another prostate-associated protein that has been linked to prostate cancer (Partin A. W. et al., 1999, Urology 54(5): 839-845; Darson M. F. et al., 1999, Urology 53(5): 939-944).

Researchers have also associated the presence of prostate-specific markers with breast tissue and/or breast secretions (Yu H. & Berkel H., 1999, J. La. State Med. Soc. 151(4): 209-213). For example, detection of PSA in benign or malignant breast tumors and breast cyst fluids has been demonstrated (Diamandis, E. P. et al., 1994, Breast Cancer Res. Treat. 32: 291-300; Yu, H. et al., 1994, Clin. Biochem. 27: 75-79; Monne, M. et al., 1994, Cancer Res. 54: 6344-6347; Malatesta M. et al., 1999, Breast Cancer Res. Treat. 57(2): 157-163; Romppanen J. et al., 1999, Br. J. Cancer 79(9-10):1583-1587). Human kallikrein-2 is also expressed in breast tumors and normal breast secretions (Black M. H. et al., 2000, Br. J. Cancer 82(2): 361-367). Breast cancer affects about 10% of the U.S. female population and, therefore, detection of cancer markers associated with the disease has clinical utility.

Determining whether a cancer, such as prostate or breast cancer, is organ-confined, locally invasive (i.e., for prostate cancer, penetrating the capsule or seminal vesicle) or has metastasized to distant sites has significant impact on both the prognosis and determining the appropriate treatment of the cancer. Therefore, effective methods of detecting cancer metastasis are medically important. For example, detecting metastasis of prostate cancer to bone tissue or pelvic lymph nodes has been used in staging the progress of the disease. Metastatic prostate cancer cells at these sites may be detected by histological examination, PSA-specific immunocytology, or by reverse transcriptase-polymerase chain reaction (RT-PCR) to detect PSA mRNA (Deguchi, T. et al., 1993, Cancer Res. 53: 5350-5354). Prostate cancer cells are also presumed to be shed into the bloodstream, permitting them to disseminate to distant sites where the cells may become established as metastases. The presence of detectable prostate-specific antigen (PSA) and/or PSA-synthesizing cells in circulating blood is an abnormal situation indicative of potential prostate cancer metastases (sometimes referred to as "hematogenous micrometastasis"), although only about 0.01% of circulating solid tumor cells eventually result in a metastatic deposit (Moreno, J. G. et al., 1992, Cancer Res. 52: 6110-6112). Similarly, detecting abnormal amounts of PSA in females may indicate the presence of breast cancer (Yu H. & Berkel H., 1999, J. La. State Med. Soc. 151(4): 209-213).

Monoclonal antibodies that react with various prostate tissue antigens have been disclosed (U.S. Pat. No. 4,970,299 to Bazinet el al., U.S. Pat. No. 4,902,615 to Freeman et al., U.S. Pat. No. 4,446,122 and U.S. Re. Pat. No. 33,405 to Chu et al., U.S. Pat. No. 4,863,851 to McEwan et al., U.S. Pat. No. 5,055,404 to Ueda et al., U.S. Pat. No. 5,763,202 to Horoszewicz, and U.S. Pat. No. 5,773,292 to Bander). Monoclonal antibody-based immunoassays for measuring total PSA, free PSA (unbound to alpha-1-antichymotrypsin or "ACT"), and PSA-ACT complexes in body fluids have been disclosed for diagnostic methods to distinguish between patients with benign prostatic hyperplasia (BHP) and those with prostatic carcinoma (U.S. Pat. No. 5,614,372 to Lilja et al.; U.S. Pat. Nos. 5,698,402 and 5,710,007 to Luderer et al.). Other known immunoassays measure total serum PSA and distinguish between free PSA in serum and PSA-protein complexes which tend to be in higher concentrations in sera from prostate cancer patients (U.S. Pat. No. 5,672,480 to Dowell et al.) PSA concentrations in amniotic fluid, as determined by antibody-based assays, have also been correlated with gestational times as an indicator of fetal abnormalities (U.S. Pat. No. 5,579,534 to Diamandis).

RT-PCR detection of PSA-synthesizing cells in peripheral blood has also been correlated with stage D1 to D3 pathology, and with capsular penetration by prostate tumor cells (Moreno, J. G. et al., 1992, Cancer Res. 52: 6110-6112; Katz, A. E. et al., 1994, Urology 43: 765-775; U.S. Pat. Nos. 5,506,106, 5,688,649 and 5,674,682 to Croce et al.; Vessella, R. L. et al., 1992, Proc. Am. Soc. Cancer Res. 33: Abstract No. 2367; Diamandis, E. P. & Yu, H., 1995, Clin. Chem. 41:177-179). Generally, RT-PCR assays rely on obtaining RNA from a blood sample, reverse transcribing the RNA into cDNA, amplifying the cDNA using a pair of primers complementary to separate regions of the PSA gene, and demonstrating the presence of the amplified DNA by observing a particular size DNA on a gel. PCR amplification of DNA requires a repeated series of thermal denaturation, primer annealing and synthesis steps (U.S. Pat. Nos. 4,683, 195, 4,683,202, and 4,800159 to Mullis et al.). The amplified DNA may be further characterized by restriction endonuclease digestion, probing with a PSA-specific oligonucleotide (e.g., Southern blotting), and/or DNA sequencing. Micrometastasis of other types of solid tumors (melanoma, neuroblastoma, breast cancer, cervical cancer) has also been detected using RT-PCR assays for other cell markers (Wu, A. et al., 1990, *US & Can. Acad. Pathol. Ann. Mtg.*, Abstract No. 641.;Smith, B. et al., 1991, *Lancet* 338: 1227-1229; Naito, H. et al., 1991, *Eur. J. Cancer* 27: 762-765; Mattano, Jr., L. A. et al. 1992, *Cancer Res.* 52: 4701-4705; U.S. Pat. Nos. 5,543,296 and 5,766,888 to Sobel et al.).

PSA is a member of a group of serine proteases known as glandular kallikreins. The human kallikreins include pancreatic/renal kallikrein (hK1), prostate-specific glandular kallikrein (hK2 or HPSK), and PSA (also known as hK3) which are encoded by related genes (hKLK1, hKLK2 and hKLK3 or PSA, respectively). Because of the chemical and structural similarities of these proteins and genes, it is important to be able to distinguish the individual proteins in immunoassays and the individual genes or their corresponding mRNA in nucleic acid detection methods. Expression of hK2 has been associated with prostate and breast cancers (Black M. H. et al., 2000, *Br. J. Cancer* 82(2):361-367; Partin A. W. et al., 1999, *Urology* 54(5): 839-845; Darson M. F. et al., 1999, *Urology* 53(5): 939-944). Antibodies that react specifically with human prostate-specific glandular kallikrein (anti-hK2) but not with PSA have been described (U.S. Pat. No. 5,516,639 to Tindall et al.; U.S. Pat. No. 5,786,148 to Bandman et al.). The gene sequences for human kallikreins are known (U.S. Pat. No. 5,786,148 to Bandman et al.; GenBank Accession Nos. NM005551, M21895, M27274, M24543, M21897, M26663, M21896, S75755, U17040, S39329 and M18157).

Some nucleic acid sequences useful for amplification of PSA mRNA in RT-PCR assays and detection of DNA products have been described (e.g., in Deguchi, T. et al., 1993, *Cancer Res.* 53:5350-5354; Katz, A. E. et al., 1994, *Urology* 43: 765-775; Moreno, J. G. et al., 1992, *Cancer Res.* 52: 6110-6112; U.S. Pat. Nos. 5,506,106, 5,688,649 and 5,674,682 to Croce et al.). Detection of prostate-associated genetic markers (e.g., PSA, PSMA and/or hK2) at locations outside of prostate tissue is useful for detecting cancer metastases, particularly prostate cancer in men and breast cancer in men and women, thereby indicating appropriate treatment. Thus, there exists a clinical need for nucleic acid sequences and methods that are used to specifically detect the presence of genetic expression of prostate-associated genetic markers, i.e., specific mRNA sequences that provide diagnostic information. There is a particular need for detecting these prostate-associated marker mRNA at levels useful for detecting relatively few cells containing the mRNA in a biological sample, such as occur in micrometastases.

SUMMARY OF THE INVENTION

The present invention is directed to assay methods for detecting and/or quantifying nucleic acids that encode prostate-specific antigen (PSA), particularly mRNA, in a non-prostate biological sample. In particular, the present invention includes preferred nucleic acid sequences useful for amplifying and hybridizing to amplified PSA-specific nucleic acids.

According to one aspect of the invention, there is provided an oligonucleotide having the sequence of any one of SEQ ID NO:1 to SEQ ID NO:43.

Another aspect of the invention is an oligonucleotide comprising a target-binding sequence consisting of the sequence of any one of SEQ ID NO:15 to SEQ ID NO:43, and optionally a contiguous sequence required for an amplification reaction. In preferred embodiments, the contiguous sequence required for an amplification reaction is a sequence that is a polymerase binding sequence, and more preferably, the polymerase binding sequence binds a T7 RNA polymerase. Preferred embodiments are oligonucleotides having the sequence is any one of SEQ ID NO:1 to SEQ ID NO:14.

Another aspect of the invention is a combination of oligonucleotides used in a detection assay specific for a prostate specific antigen (PSA) target nucleic acid sequence. The combination comprises a first oligonucledtide that serves as a first amplification primer that hybridizes specifically to a first PSA-specific sequence contained in an exon of a PSA expressed gene sequence, or that spans a joining point linking two exons of a PSA expressed gene sequence; a second oligonucleotide that serves as a second amplification primer that specifically hybridizes to a different, non-overlapping second PSA-specific sequence contained in an exon of a PSA expressed gene sequence, or that spans a joining point linking two exons of a PSA expressed gene sequence; and a third oligonucleotide that serves as a detection probe that specifically hybridizes to a third PSA-specific sequence contained in one or more exons of a PSA expressed gene sequence. Preferably, the first PSA-specific sequence is contained in PSA exon 2, exon 3 or exon 4, or is a sequence that spans a joining point linking exons 2 and 3 or exons 3 and 4. Preferably, the second PSA-specific sequence is contained in PSA exon 3, exon 4 or exon 5, or is a sequence that spans a joining point linking exons 3 and 4 or exons 4 and 5. Preferably, the third PSA-specific sequence is contained within PSA exon 2, exon 3, exon 4 or exon 5, or spans a joining point that links PSA exons 2 and 3, exons 3 and 4, or exons 4 and 5. Particularly preferred combinations of oligonucleotides are a first oligonucleotide comprising a sequence selected from the group consisting of SEQ ID NO:15, SEQ ID NO:16, SEQ ID NO:18, SEQ ID NO:20, SEQ ID NO:21 and SEQ ID NO:26; the second oligonucleotide comprising a sequence selected from the group consisting of SEQ ID NO:30, SEQ ID NO:31, SEQ ID NO:32, SEQ ID NO:33, SEQ ID NO:34, SEQ ID NO:35, SEQ ID NO:37, SEQ ID NO:38, SEQ ID NO:40 and SEQ ID NO:41; and the third oligonucleotide comprises a sequence selected from the group consisting of SEQ ID NO:1, SEQ ID NO:2, SEQ ID NO:3, SEQ ID NO:4, SEQ ID NO:5, SEQ ID NO:6, SEQ ID NO:8, and SEQ ID NO:14. Additional preferred combinations of first, second and third oligonucleotides, in that order, have sequences of:
SEQ ID NO:15, SEQ ID NO:30 and SEQ ID NO:1;
SEQ ID NO:17, SEQ ID NO:30 and SEQ ID NO:1;
SEQ ID NO:18, SEQ ID NO:30 and SEQ ID NO:1;
SEQ ID NO:18, SEQ ID NO:35 and SEQ ID NO:1;
SEQ ID NO:18, SEQ ID NO:30 and SEQ ID NO:4;
SEQ ID NO:18, SEQ ID NO:30 and SEQ ID NO:5;
SEQ ID NO:18, SEQ ID NO:30 and SEQ ID NO:6;
SEQ ID NO:16, SEQ ID NO:31 and SEQ ID NO:2;
SEQ ID NO:16, SEQ ID NO:31 and SEQ ID NO:3;
SEQ ID NO:16, SEQ ID NO:33 and SEQ ID NO:2;
SEQ ID NO:16, SEQ ID NO:33 and SEQ ID NO:3;
SEQ ID NO:16, SEQ ID NO:32 and SEQ ID NO:2;
SEQ ID NO:16, SEQ ID NO:32 and SEQ ID NO:3;
SEQ ID NO:16, SEQ ID NO:34 and SEQ ID NO:2;
SEQ ID NO:16, SEQ ID NO:34 and SEQ ID NO:3;
SEQ ID NO:20, SEQ ID NO:37 and SEQ ID NO:8;
SEQ ID NO:20, SEQ ID NO:38 and SEQ ID NO:8;

SEQ ID NO:21, SEQ ID NO:37 and SEQ ID NO:8;
SEQ ID NO:21, SEQ ID NO:38 and SEQ ID NO:8;
SEQ ID NO:21, SEQ ID NO:40 and SEQ ID NO:14;
SEQ ID NO:21, SEQ ID NO:37 and SEQ ID NO:14;
SEQ ID NO:21, SEQ ID NO:41 and SEQ ID NO:14;
SEQ ID NO:21, SEQ ID NO:40 and SEQ ID NO:8;
SEQ ID NO:21, SEQ ID NO:41 and SEQ ID NO:8;
SEQ ID NO:26, SEQ ID NO:37 and SEQ ID NO:8;
SEQ ID NO:26, SEQ ID NO:40 and SEQ ID NO:8; or
SEQ ID NO:26, SEQ ID NO:41 and SEQ ID NO:8.

Particularly preferred combinations of first, second and third oligonucleotides, in that order, have sequences of: SEQ ID NO:17, SEQ ID NO:30 and SEQ ID NO:1;
SEQ ID NO:18, SEQ ID NO:30 and SEQ ID NO:1;
SEQ ID NO:20, SEQ ID NO:37 and SEQ ID NO:8;
SEQ ID NO:21, SEQ ID NO:40 and SEQ ID NO:14;
SEQ ID NO:21, SEQ ID NO:41 and SEQ ID NO:14;
SEQ ID NO:26, SEQ ID NO:37 and SEQ ID NO:8;
SEQ ID NO:26, SEQ ID NO:40 and SEQ ID NO:8; or
SEQ ID NO:26, SEQ ID NO:41 and SEQ ID NO:8. In other embodiments, the combination of first, second and third oligonucleotides further includes at least one helper probe oligonucleotide. Preferred helper probe oligonucleotides included in a combination consist of an oligonucleotide having the sequence of SEQ ID NO:27 or SEQ ID NO:28, or a combination of oligonucleotides having those sequences.

Particularly preferred combinations of first, second and third oligonucleotides and helper probe oligonucleotides, in that order, have the sequences of:
SEQ ID NO:21, SEQ ID NO:41, SEQ ID NO:8 and SEQ ID NO:27;
SEQ ID NO:21, SEQ ID NO:41, SEQ ID NO:8, SEQ ID NO:27 and SEQ ID NO:28;
SEQ ID NO:26, SEQ ID NO:40, SEQ ID NO:8, SEQ ID NO:27 and SEQ ID NO:28;
SEQ ID NO:26, SEQ ID NO:37, SEQ ID NO:8, SEQ ID NO:27 and SEQ ID NO:28;
SEQ ID NO:26, SEQ ID NO:41, SEQ ID NO:8, SEQ ID NO:27 and SEQ ID NO:28;
SEQ ID NO:26, SEQ ID NO:43, SEQ ID NO:8, SEQ ID NO:27 and SEQ ID NO:28; or
SEQ ID NO:26, SEQ ID NO:38, SEQ ID NO:8, SEQ ID NO:27 and SEQ ID NO:28. More preferably, the combinations of first, second and third oligonucleotides and helper probe oligonucleotides, in that order, have sequences of:
SEQ ID NO:21, SEQ ID NO:41, SEQ ID NO:8, SEQ ID NO:27 and SEQ ID NO:28;
SEQ ID NO:26, SEQ ID NO:40, SEQ ID NO:8, SEQ ID NO:27 and SEQ ID NO:28;
SEQ ID NO:26, SEQ ID NO:37, SEQ ID NO:8, SEQ ID NO:27 and SEQ ID NO:28; or
SEQ ID NO:26, SEQ ID NO:41, SEQ ID NO:8, SEQ ID NO:27 and SEQ ID NO:28.

One aspect of the invention is a method of detecting a prostate-associated target nucleic acid in a biological sample containing nucleic acid, comprising the steps of providing a nucleic acid sample containing a target nucleic acid that includes at least a portion of at least one expressed gene sequence encoding prostate-specific antigen (PSA), prostate-specific membrane antigen (PSMA) or human kallikrein 2 (hK2); then hybridizing to the target nucleic acid at least one primer oligonucleotide containing a sequence that hybridizes specifically to the target nucleic acid or a complement thereof; producing a plurality of amplification products of the target nucleic acid by using at least one polymerase activity; providing a probe oligonucleotide that hybridizes specifically to at least one amplification product of the target nucleic acid; and detecting a signal resulting from the probe hybridized to the amplification product. In preferred embodiments the at least one primer oligonucleotide comprises the sequence of any one of SEQ ID NO:15 to SEQ ID NO:29, SEQ ID NO:46, SEQ ID NO:48, or a target-binding sequence of any one of SEQ ID NO:30 to SEQ ID NO:43, SEQ ID NO:47 or SEQ ID NO:49. In one embodiment, the target nucleic acid is a PSA mRNA; the at least one primer oligonucleotide comprises a promoter-primer oligonucleotide consisting of a sequence complementary to at least a portion of the PSA mRNA and a sequence that is a promoter sequence, and at least one primer oligonucleotide that hybridizes specifically to a nucleic acid strand complementary to the PSA mRNA; and the probe oligonucleotide hybridizes specifically to amplification products of a sense that is the same as that of the PSA mRNA. Preferably, the promoter-primer oligonucleotide comprises the sequence of any one of SEQ ID NO:30 to SEQ ID NO:43, and the primer oligonucleotide that hybridizes specifically to a nucleic acid strand complementary to the PSA mRNA comprises the sequence of any one of SEQ ID NO:15 to SEQ ID NO:29. In another embodiment, the target nucleic acid is a PSMA mRNA; the at least one primer oligonucleotide comprises a promoter-primer oligonucleotide consisting of a sequence complementary to at least a portion of the PSMA mRNA and a sequence that is a promoter sequence, and at least one primer oligonucleotide that hybridizes specifically to a nucleic acid strand complementary to the PSMA mRNA; and the probe oligonucleotide hybridizes specifically to amplification products of a sense that is the same as that of the PSMA mRNA. Preferably, the promoter-primer oligonucleotide comprises the sequence of SEQ ID NO:49, and the primer oligonucleotide that hybridizes specifically to amplification products of a sense that is the same as that of the PSMA mRNA comprises the sequence of SEQ ID NO:48. In another embodiment, the target nucleic acid is a hK2 mRNA; the at least one primer oligonucleotide comprises a promoter-primer oligonucleotide consisting of a sequence complementary to at least a portion of the hK2 mRNA and a sequence that is a promoter sequence, and at least one primer oligonucleotide that hybridizes specifically to a nucleic acid strand complementary to the hK2 mRNA; and the probe oligonucleotide hybridizes specifically to amplification products of a sense that is the same as that of the hK2 mRNA. Preferably, in the method, the promoter-primer oligonucleotide comprises the sequence of SEQ ID NO:47, and the primer oligonucleotide that hybridizes specifically to amplification products of a sense that is the same as that of the hK2 mRNA comprises the sequence of SEQ ID NO:46. Preferably, the detecting step uses at least one probe oligonucleotide consisting of a sequence of any one of SEQ ID NO:1 to SEQ ID NO:14, SEQ ID NO:27, SEQ ID NO:28 or SEQ ID NO:50. One embodiment of the method comprises assaying for the expressed gene sequence encoding PSA and at least one expressed gene sequence encoding PSMA or hK2. In preferred embodiments, the nucleic acid sample is RNA, more preferably mRNA, isolated from human prostate tissue, peripheral blood, breast tissue, kidney tissue, small intestine, lung tissue, liver tissue or lymph node. In preferred embodiments, the detecting step detects a signal in a homogeneous detection assay.

DETAILED DESCRIPTION OF THE INVENTION

The present invention includes nucleic acid sequences specific for segments of a human PSA gene which are used in methods of detecting PSA-specific sequences in nucleic acids prepared from a biological sample that is not taken from prostate tissue. The invention further includes nucleic acid sequences specific for segments of other prostate-associated genetic markers, a human PSMA gene and hK2 gene, which are used in methods of detecting prostate-associated sequences that are useful cancer detection markers in nucleic acids prepared from a biological sample of non-prostate tissue, including breast tissue. The non-prostate tissue can include, for example, blood, lymph node, breast or breast cyst, kidney, liver, lung, muscle, stomach or intestinal tissue. The invention also includes preferred methods that combine nucleic acid sequences for amplifying and detecting PSA-specific sequences, PSMA and/or hK2 sequences, individually or in combination, in non-prostate tissue. The preferred methods amplify PSA, PSMA and/or hK2 mRNA sequences without requiring thermal cycling and detect the amplified sequences in a homogeneous assay system. The methods may optionally include a simplified method of preparing RNA samples derived from non-prostate tissue samples, such as peripheral blood, lymph nodes or bone marrow, although other non-prostate tissues may be used. The preferred RNA preparation method is relatively simple and provides RNA suitable for analysis and detection of mRNA species that occur in relatively low abundance in the biological samples.

Figure 1:
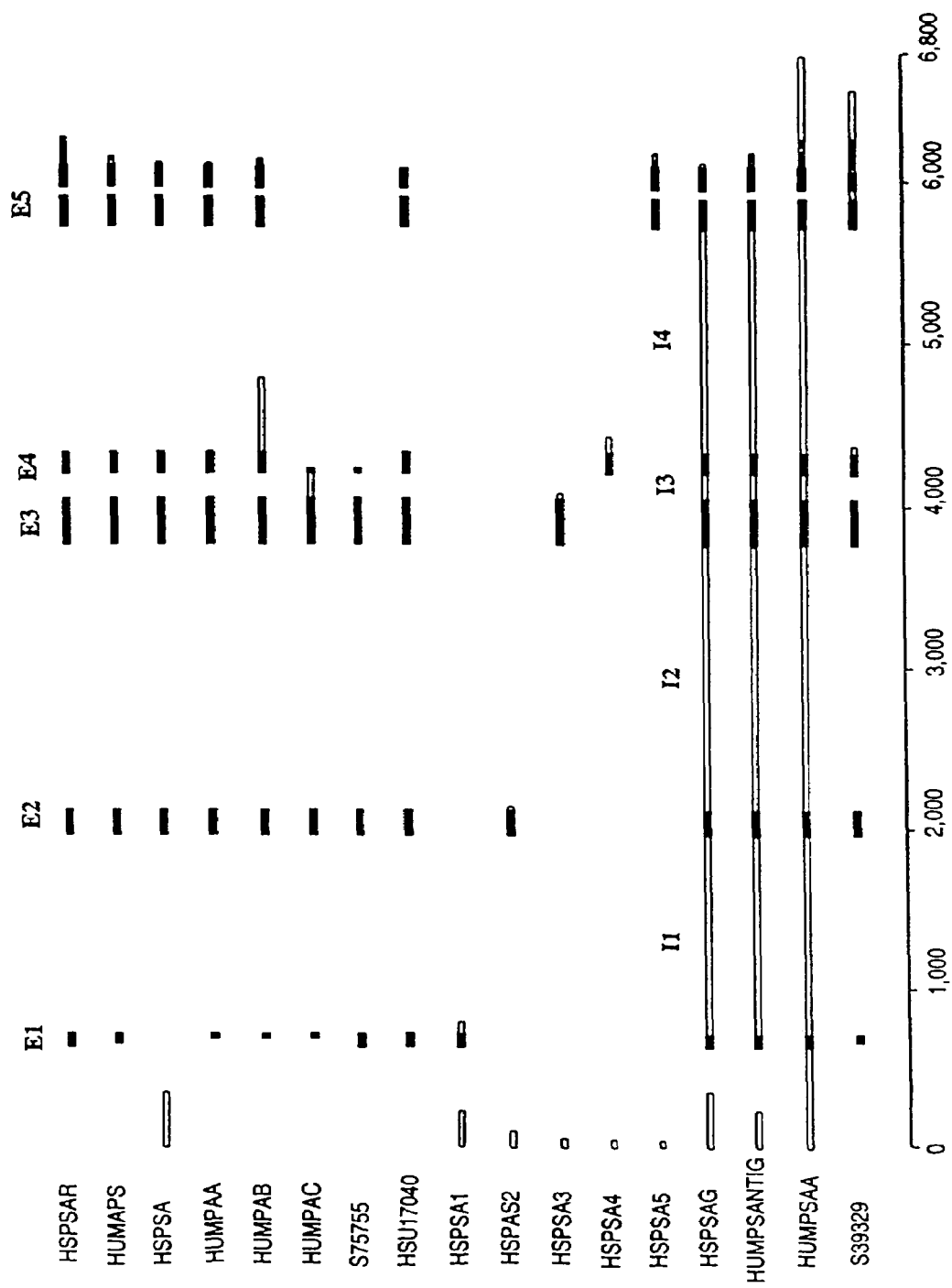
FIG. 1 is a schematic drawing showing the PSA gene structure and alignment of various PSA and kallikrein-1 sequences available from GenBank and or EMBL using the accession numbers (Acc. No.) provided below, where the closed boxes (■) indicate exons 1 to 5 ("E1", "E2", "E3", "E4" and "E5") and the open boxes (□) indicate introns ("I1", "I2", "I3" and "I4" are specifically labeled, whereas introns preceding the first exon or following the last exon are not labeled), presented over a scale representing the number of bases from 0 to 6,800 to show the relative positions of the introns and exons. The diagramed known PSA gene sequences are labeled: "HSPSAR" (1,466 bp; Acc. No. X05332), "HUMAPS" (1,446 bp; Acc. No. M26663), "HSPSA" (1,729 bp; Acc. No. X07730), "HUMPAA" (1,415 bp; Acc. No. M21895), "HUMPAB" (1,654 bp; Acc.No. M21896), "HUMPAC" (658 bp; Acc. No. M21897), "S75755" (569 bp; Acc. No. S75755), "HSU17040" (990 bp; Acc. No. U17040), "HSPSA1" (389 bp; Acc No. X13940), "HSPSA2" (287 bp; Acc. No. X13941), "HSPSA3" (372 bp; Acc. No.X13942), "HSPSA4" (281 bp; Acc. No. X13943), "HSPSA5" (900 bp; Acc. No. X13944), "HSPSAG" (5,873 bp; Acc. No. X14810), "HUMPSANTIG" (6,153 bp; Acc. No. M24543), and "HUMPSAA" (7,130 bp; Acc. No. M27274), and the human glandular kallikrein-1 sequence "S39329" (1,541 bp; Acc. No. S39329).

The sequence of the human PSA gene is known and is available in a number of databases (GenBank and EMBL databases, in Accession Nos. AF007544, X05332, M26663, X07730, M21895, M21896, M21897, S75755, U17040, X13942, X14810, M24543, M27274; accession numbers beginning with "X" indicate sequences in the EMBL database). The sequence of the related gene for the human glandular kallikrein-1 is known (Acc. No. S39329) as is the human prostate-specific membrane antigen sequence (GenBank Acc. No. M99487). As shown in FIG. 1, the PSA and kallikrein-1 genes share similar-structural characteristics, which include five exons (labeled E1 to E5) separated by four internal introns (labeled I1 to I4). The entire PSA gene sequence, including untranslated 5' and 3' regions, spans about 6.8 kb. Because of the structural and sequence similarities of the PSA gene and the other members of the kallikrein gene family, the appropriate selection of PSA sequences to serve as PSA-specific primers and probes is critical to methods of amplifying and detecting PSA-specific nucleic acids in non-prostate tissue samples (i.e., to avoid false positives resulting from amplification and/or detection of kallikrein nucleic acids). Preferred probes, primers and promoter-primers of the present invention used for detecting PSA-specific sequences are shown in Table 1 (with their SEQ ID NOs).

TABLE 1

| SEQ ID NO: | Nucleic Acid Sequence | Length | PSA Location |
|---|---|---|---|
| 1 | GGACCACCTGCTACGCCTCAG | 21 | Exon 3 |
| 2 | GACCAAGTTCATGCTGTGTGCTG | 23 | Exon 4 |
| 3 | GACCAAGTTCATGCTGTGTGCTG | 23 | Exon 4 |

TABLE 1-continued

| SEQ ID NO: | Nucleic Acid Sequence | Length | PSA Location |
|---|---|---|---|
| 4 | GCTGTGAAGGTCATGGACCTGCC | 23 | Exon 3 |
| 5 | GAACCAGAGGAGTTCTTGACCC | 22 | Exon 3/4 |
| 6 | GGCCAGATGGTGCAGCCGGGAGC | 23 | Intron 3 |
| 7 | GCAGTCTGCGGCGGTGTTCTG | 21 | Exon 2 |
| 8 | ACAGCTGCCCACTGCATCAGG | 21 | Exon 2 |
| 9 | GTTCACCCTCAGAAGGTGACC | 21 | Exon 4 |
| 10 | GCTGTGTGCTGGACGCTGGAC | 21 | Exon 4 |
| 11 | GCTTGTGGCCTCTCGTGGCAG | 21 | Exon 2 |
| 12 | TGGCCTCTCGTGGCAGGGCAGT | 22 | Exon 2 |
| 13 | TCTCGTGGCAGGGCAGTCTGC | 21 | Exon 2 |
| 14 | GTGCACCCCAGTGGGTCCTC | 21 | Exon 2 |
| 15 | GATGCTGTGAAGGTCATGGACCTG | 24 | Exon 3 |
| 16 | GTGCGCAAGTTCACCCTCAGAAGG | 24 | Exon 4 |
| 17 | GAAGGTCATGGACCTGCCCACCCA | 24 | Exon 3 |
| 18 | CTGTCAGAGCCTGCCGAGCTCACG | 24 | Exon 3 |
| 19 | GCTGCTCCGCCTGTCAGAGCCTG | 23 | Exon 3 |
| 20 | GCTTGTGGCCTCTCGTGGCAG | 21 | Exon 2 |
| 21 | TCTCGTGGCAGGGCAGTCTGC | 21 | Exon 2 |
| 22 | TTCCAATGACGTGTGTGCGCA | 21 | Exon 4 |
| 23 | GGAGGCTGGGAGTGCGAGAAGCAT | 24 | Exon 2 |
| 24 | GGCTGGGAGTGCGAGAAGCATT | 22 | Exon 2 |
| 25 | TGGCCTCTCGTGGCAGGGCAGT | 22 | Exon 2 |
| 26 | GCAGTCTGCGGCGGTGTTCTG | 21 | Exon 2 |
| 27 | GTGCACCCCAGTGGGTCCTC | 21 | Exon 2 |
| 28 | AACAAAAGCGTGATCTTGCTGGG | 23 | Exon 2/3 |
| 29 | CAAAAGCGTGATCTTGCTGGGT | 22 | Exon 3 |
| 30 | TAAATTAATACGACTCACTATAGGGAGA CCAGAGGGTGAACTTGCGCACACACG | 54 | Exon 4 |
| 31 | TAAATTAATACGACTCACTATAGGGAGA CTGCACCACCTTGGTGTACAGG | 50 | Exon 5 |
| 32 | TAAATTAATACGACTCACTATAGGGAGA CTCATGGTTCACTGCCCCATGACGTG | 54 | Exon 5 |
| 33 | AATTTAATACGACTCACTATAGGGAGA TGCACCACCTTGGTGTACAGG | 48 | Exon 5 |
| 34 | AATTTAATACGACTCACTATAGGGAGA CATGGTTCACTGCCCCATGACGTG | 51 | Exon 5 |
| 35 | AATTTAATACGACTCACTATAGGGAGA GAGGGTGAACTTGCGCACACACG | 50 | Exon 3 |
| 36 | TAAATTAATACGACTCACTATAGGGAGA CCACCTTCTGAGGGTGAACTTGCG | 52 | Exon 4 |
| 37 | TAAATTAATACGACTCACTATAGGGAGA GCCGACCCAGCAAGATCACGC | 49 | Exon 3 |
| 38 | TAAATTAATACGACTCACTATAGGGAGA CTGTGGCTGACCTGAAATACC | 49 | Exon 3 |
| 39 | TAAATTAATACGACTCACTATAGGGAGA GTGTACAGGGAAGGCCTTTCG | 49 | Exon 5 |
| 40 | TAAATTAATACGACTCACTATAGGGAGA ACCCAGCAAGATCACGCTTTTG | 50 | Exon 3 |
| 41 | TAAATTAATACGACTCACTATAGGGAGA AGGCTGTGCCGACCCAGCAAGAT | 51 | Exon 3 |
| 42 | TAAATTAATACGACTCACTATAGGGAGA CCTGTGTCTTCAGGATGAAACAGG | 52 | Exon 3 |
| 43 | TAAATTAATACGACTCACTATAGGGAGA CTGACCTGAAATACCTGGCCTGTG | 52 | Exon 3 |

Figure 2:
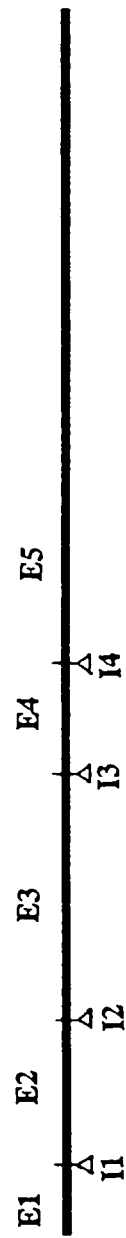
FIG. 2 is a schematic drawing showing the relative locations of various probes of the present invention (listed on the left using SEQ ID NO.) over a solid line representing the majority of the expressed PSA gene (based on the 1,466 bp sequence of HSPSAR, Acc. No. X05332) with the locations of exons 1-5 (labeled E1, E2, E3, E4, and E5) shown above the solid line and the splice junctions of deleted introns 1-4 (labeled I1, I2, I3, and I4) shown below the solid line.
Figure 3:
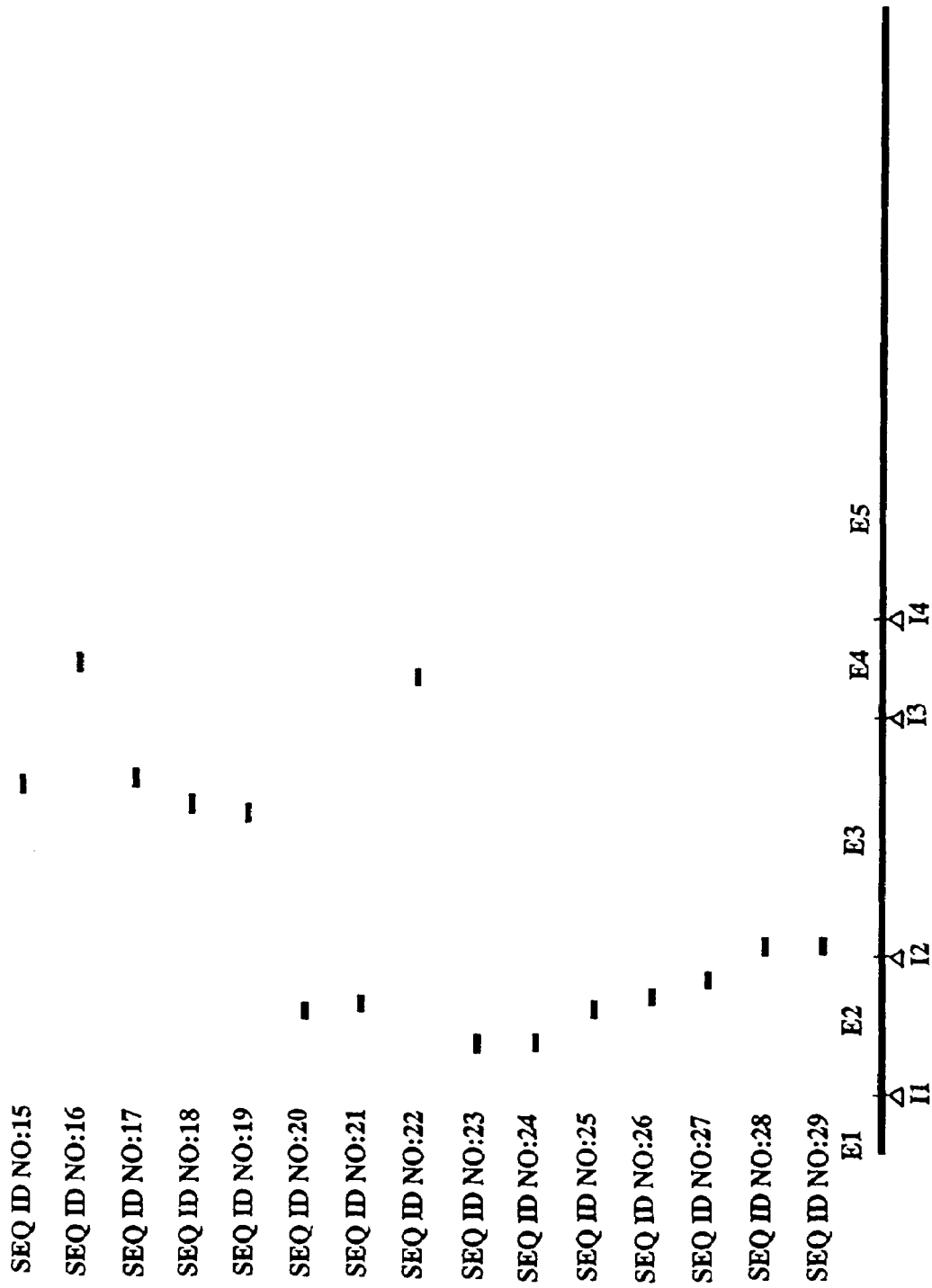
FIG. 3 is a schematic drawing showing the relative locations of various probes of the present invention (listed on the left using SEQ ID NO.) over a solid line representing the majority of the expressed PSA gene (based on the 1,466 bp sequence of HSPSAR, Acc. No. X05332) with the locations of exons 1-5 (labeled E1, E2, E3, E4, and E5) shown above the solid line and the splice junctions of deleted introns 1-4 (labeled I1, I2, I3, and I4) shown below the solid line.
Figure 4:
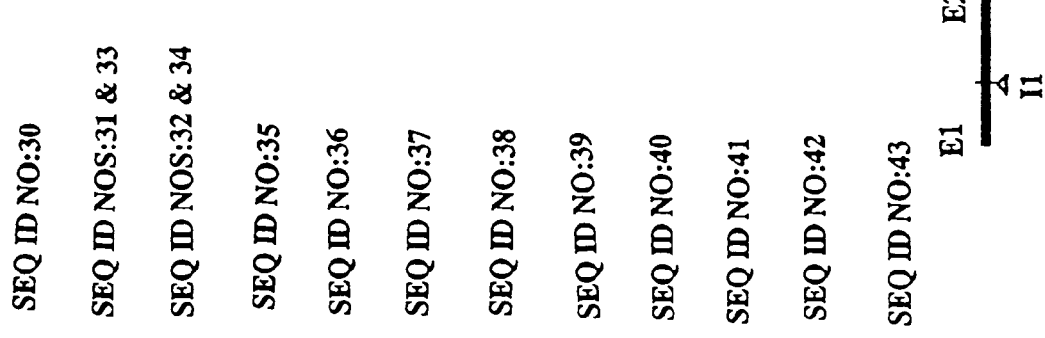
FIG. 4 is a schematic drawing showing the relative locations of various probes of the present invention (listed on the left using SEQ ID NO.) over a solid line labeled "HSPSAR" representing the majority of the expressed PSA gene (based on the 1,466 bp sequence of HSPSAR,.Acc. No. X05332) with the locations of exons 1-5 (labeled E1, E2, E3, E4, and E5) shown above the solid line and the splice junctions of deleted introns 1-4 (labeled I1, I2, I3, and I4) shown below the solid line.

FIGS. 2 to 4 show the relative locations of these sequences compared to the expressed human PSA gene sequences (1,466 bp sequence of HSPSAR, Acc. No. X05332), diagramed with the relative locations of the exons and intron splice sites at the bottoms of the figures. Referring to FIG. 2, the relative locations of probes having sequences of SEQ ID NO:1 to SEQ ID NO:5 and SEQ ID NO:7 to SEQ ID NO:14 are shown. These preferred probes are specific for PSA sequences in exons 2, 3 and 4. A probe specific for a PSA intron 3 sequence (SEQ ID NO:6) is not shown on FIG. 2. Referring to FIG. 3, the relative locations of primers having sequences of SEQ ID NO:15 to SEQ ID NO:29 are shown. These preferred primers are specific for PSA sequences in exons 2, 3, 4, and spanning exons 2 and 3, including the splice junction (SEQ ID NO:28). Referring to FIG. 4, the relative locations of target-binding sequences of promoter-primers having sequences of SEQ ID NO:30 to SEQ ID NO:43 are shown. These preferred target-binding sequences are specific for PSA sequences in exons 3, 4 and 5.

For amplifying and detecting hK2 sequences, a preferred primer has the sequence GTCAGAGCCTGCCAAGATCACAG (SEQ ID NO:46) and a preferred promoter-primer has the sequence TAAATTAATACGACTCACTATAGGGAGACCACCAGCACACAACATGAACTCTGTC (SEQ ID NO:47). A labeled probe suitable for detecting the amplified hK2 sequences uses the sequence of SEQ ID NO:1 shown in Table 1.

For amplifying and detecting PSMA sequences, a preferred primer has the sequence CAGATATGTCATTCTGGGAGGTC (SEQ ID NO:48) and a preferred promoter-primer has the sequence TAAATTAATACGACTCACTATAGGGAGACCAAATTCTTCTGCATCCCAGCTTGC (SEQ ID NO:49), and a labeled probe that includes the sequence CTCAGAGTGGAGCAGCTGTTGTTC (SEQ ID NO:50).

The present invention also includes a method for detecting and quantifying the PSA-specific RNA species, which is particularly important because these mRNA species occur in relatively low abundance in RNA samples prepared from non-prostate tissues. Other embodiments of the invention include methods for detecting prostate-associated PSMA and hK2 RNA species, which when detected individually or in combination with each other or PSA sequences, are important because these also are cancer markers for prostate and breast cancer when found in non-prostate tissues. More-over, detection of these prostate-associated markers (PSA, PSMA and hK2), individually and in combination, are clinically important because cancers from individual patients may express one or more of the markers, such that detecting one or more of the markers decreases the potential of false negatives during diagnosis that might otherwise result if the presence of only one marker was tested. These methods are useful for medical diagnoses without requiring a prostate biopsy and for clinically monitoring a patient's response to therapy for prostate cancer. Because the methods are sufficiently sensitive to detect the presence of relatively low levels of prostate-associated RNA, such as PSA-specific mRNA, they are useful for detecting recurrence or metastasis of prostate and/or breast cancer. Another advantage of the present methods is that amplification primers specific for different exons of a target sequence will amplify only mRNA that have been spliced to link the exons in proximity, thereby eliminating amplification and false positive detection that might result from contaminating genomic DNA in the biological sample. In such an embodiment of the method, detection of genomic DNA is precluded because the exons in the genomic sequence are separated by intron sequence(s) such that the entire region between the two primer binding sites will not be efficiently amplified and, therefore, will not be detected.

The invention also includes preferred combinations of nucleic acid sequences for amplifying and detecting human prostate-associated genetic markers, including those specific for PSA, PSMA and hK2 nucleic acid sequences.

In addition to definitions provided elsewhere in the specification, some terms have been defined as follows. Unless indicated or defined otherwise, all scientific and technical terms used herein have the same meaning as commonly understood by those skilled in the relevant art. General definitions of many terms used herein are provided in *Dictionary of Microbiology and Molecular Biology*, 2nd ed. (Singleton et al., 1994, John Wiley & Sons, New York, N.Y.), *The Harper Collins Dictionary of Biology* (Hale & Marham, 1991, Harper Perennial, New York, N.Y.), and *Dorland's Illustrated Medical Dictionary*, 27th ed. (W. A. Dorland, 1988, W. B. Saunders Co., Philadelphia, Pa.).

By "nucleotide sequence" or "nucleic acid sequence" is meant the sequence of nitrogenous bases along a linear information-containing molecule that is capable of hydrogen-bonding with another nucleic acid strand of DNA or RNA having a complementary base sequence. The terms are not meant to limit such information-containing molecules to polymers of nucleotides per se but also include molecule structures containing one or more nucleotide analogs or abasic units in the polymer. The polymers may include base subunits containing a sugar moiety or a substitute for ribose or deoxyribose (for example, 2' halide- or methoxy-substituted pentose sugars), and may be linked by linkages other than phosphodiester bonds, such as phosphorothioate, methylphosphonate, and peptide linkages.

By "oligonucleotide" is meant a polymeric chain of two or more chemical subunits, each subunit comprising a nucleotide base moiety, a sugar moiety, and a linking moiety which joins the subunits in a linear spacial configuration. An oligonucleotide may contain up to thousands of such subunits, but generally contains subunits in a range having a lower limit of between about 5 to about 10 subunits, and an upper range between about 20 to about 1,000 subunits. The most common nucleotide base moieties are guanine (G), adenine (A), cytosine (C), thymine (T) and uracil (U), although other rare or modified nucleotide bases able to form hydrogen bonding (e.g., inosine or 1) are well known to those skilled in the art. The most common sugar moieties are ribose and deoxyribose, although 2'-O-methyl ribose, halogenated sugars, and other modified and different sugars are well known. The linking group is usually a phosphorus-containing moiety, commonly a phosphodiester linkage, although other known phosphate-containing linkages (e.g., phosphorothioates, methylphosphonates) and non-phosphorus-containing linkages (e.g. peptide-like linkages found in "peptide nucleic acids" or PNA) known in the art are included. Thus, PNA are intended to fall within this definition of an oligonucleotide. Likewise, an oligonucleotide includes one in which at least one base moiety has been modified, for example, by the addition of propyne groups, so long as (1) the modified base moiety retains the ability to form a non-covalent association with G, A, C, T or U, and (2) an oligonucleotide comprising at least one modified nucleotide base moiety is not sterically prevented from hybridizing with a complementary single-stranded nucleic acid. An oligonucleotide's ability to hybridize with a complementary nucleic acid strand under particular conditions (e.g., temperature, salt concentration) is governed by the sequence of base moieties, as is well known to those skilled in the art (Sambrook, J. et al., 1989, *Molecular Cloning, A Laboratory Manual*, $2^{nd}$ ed. (Cold Spring Harbor Laboratory Press, Cold Spring Harbor, N.Y., particularly pp. 7.37-7.57 and 11.47-11.57).

By "amplification" is meant production of multiple copies of a target nucleic acid that contains at least a portion of a the intended specific target nucleic acid sequence (PSA, PSMA or hK2). The multiple copies may be referred to as amplicons or amplification products. Preferably, the amplified target contains less than the complete target gene sequence (introns and exons) or an expressed target gene sequence (spliced transcript of exons and flanking untranslated sequences). For example, PSA-specific amplicons may be produced by amplifying a portion of the PSA target polynucleotide by using amplification primers which hybridize to, and initiate polymerization from, internal positions of the PSA target polynucleotide. Preferably, the amplified portion contains a detectable target sequence which may be detected using any of a variety of well known methods.

By "nucleic acid amplification conditions" is meant environmental conditions including salt concentration, temperature, the presence or absence of temperature cycling, the presence of a nucleic acid polymerase, nucleoside triphosphates, and cofactors which are sufficient to permit the production of multiple copies of a target nucleic acid or its complementary strand using a nucleic acid amplification method. Many well-known methods of nucleic acid amplification require thermocycling to alternately denature double-stranded nucleic acids and hybridize primers. For example, the polymerase chain reaction or PCR (U.S. Pat. Nos. 4,683,195; 4,683,202; 4,800,159; 4,965,188) uses multiple cycles of denaturation, annealing of a pair of primers to opposite strands, and primer extension lead to exponential increases in copies of the target sequence. In a variation called RT-PCR, reverse transcriptase (RT) is used to make a complementary DNA (cDNA) from mRNA, and the cDNA is then amplified by PCR to produce multople copoies of DNA. The ligase chain reaction or LCR (Weiss, R. 1991, *Science* 254: 1292) uses two sets of complementary DNA oligonucleotides which hybridize to adjacent regions of the target nucleic acid and are covalently linked by using a DNA ligase, in repeated cycles of thermal denaturation, hybridization and ligation, to produce a detectable double-stranded ligated oligonucleotide product. Another method is strand displacement amplification or SDA (Walker, G. et al., 1992, *Proc. Natl. Acad. Sci.* USA 89:392-396; U.S. Pat. Nos. 5,270,184 and 5,455,166) which uses cycles of annealing pairs of primer sequences to opposite strands of a target sequence, primer extension in the presence of a dNTP[α]S to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA or tSDA uses thermophilic endonucleases and polymerases at higher temperatures in essentially the same method (European Pat. App. 0 684,315). Other amplification methods include nucleic acid based sequence amplification or NASBA (U.S. Pat. No. 5,130, 238), one that uses an RNA replicase (Qβ replicase) to amplify the probe molecule itself (Lizardi, P. et al., 1988, *BioTechnol.* 6: 1197-1202), a transcription based amplification method (Kwoh, D. et al., 1989, *Proc. Natl. Acad. Sci.* USA 86: 1173-1177), self-sustained sequence replication (Guatelli, J. et al., 1990, *Proc. Natl. Acad. Sci.* USA 87: 1874-1878), and transcription mediated amplification (U.S. Pat. Nos. 5,480,784 and 5,399,491 to Kacian & Fultz) which produces multiple RNA transcripts of the target sequence. For further discussion of known amplification methods, see Persing, David H., 1993, "In Vitro Nucleic Acid Amplification Techniques" in *Diagnostic Medical Microbiology: Principles and Applications* (Persing et al., Eds.,), pp. 51-87 (American Society for Microbiology, Washington, D.C.).

Preferred transcription based amplification systems of the present invention employ an RNA polymerase to make many RNA transcripts of a target region (U.S. Pat. Nos. 5, 480,784 and 5,399,491 to Kacian & Fultz). Transcription mediated amplification (TMA) uses a promoter-primer that hybridizes to a target nucleic acid in the presence of a reverse transcriptase and an RNA polymerase to form a double stranded promoter. Then, RNA polymerase activity produces RNA transcripts that can become templates for further rounds of TMA in the presence of a second primer capable of hybridizing to the RNA transcripts. Unlike PCR, LCR or other methods that require heat denaturation, TMA is an isothermal method that uses an RNAse H activity to digest the RNA strand of an RNA-DNA hybrid, thereby making the DNA strand available for hybridization with a primer or promoter-primer. Generally, the RNAse H activity associated with a retroviral reverse transcriptase provided for amplification is used.

By "primer" or "amplification primer" is meant an oligonucleotide capable of binding to a region of a target nucleic acid or its complement and promoting nucleic acid amplification of the target nucleic acid. In most cases a primer will have a free 3' end which can be extended by a nucleic acid polymerase. All amplification primers include a base sequence capable of hybridizing via complementary base interactions either directly with at least one strand of the target nucleic acid or with a strand that is complementary to the target sequence. Amplification primers serve as substrates for enzymatic activity that produces a longer nucleic acid product.

For example, in PCR, amplification primers anneal to opposite strands of a double stranded target DNA that has been denatured and the primers are extended by a thermostable DNA polymerase to produce double-stranded DNA products which are denatured with heat, cooled and annealed to the amplification primers, and the primers are extended by polymerase activity during multiple cycles (e.g., about 20 to about 50 thermic cycles).

In another example, in TMA, one amplification primer is a "promoter-primer" that hybridizes to a target RNA and reverse transcriptase (RT) produces a cDNA copy of the target RNA, while RNase H activity degrades the target RNA. The promoter-primer is an oligonucleotide that comprises a promoter sequence (which become functional when double stranded) located to 5' of a target-binding sequence which is capable of hybridizing to the target sequence. The target-binding sequence is capable of hybridizing to a binding site of the target RNA at a location 3' to the sequence to be amplified. When made double-stranded, the promoter sequence is capable of binding an RNA polymerase to begin transcription of the target sequence to which the promoter primer is hybridized. A promoter-primer may be referred to as a "T7-primer" when it is specific for T7 RNA polymerase recognition. Under certain circumstances the 3' end of a promoter-primer, or a subpopulation of such promoter-primers, may be modified to block or reduce primer extension. A second amplification primer then binds to the cDNA and RT produces another DNA strand resulting in a double-stranded DNA containing a functional RNA promoter at one end. The second amplification primer comprises a target-binding sequence capable of hybridizing to the complement (i.e., the cDNA strand) of the target RNA. It may be referred to as a "non-T7 primer" to distinguish it from a "T7-primer" An RNA polymerase uses this promoter sequence to produce multiple RNA transcripts (i.e., amplicons), generally about 100 to 1,000 copies. Each newly-synthesized amplicon can anneal with the second amplification primer which is extended by RT to produce a DNA copy, while the RNase H activity degrades the RNA of this RNA:DNA duplex. The promoter-primer then binds to the newly synthesized DNA and RT creates a double-stranded DNA from which the RNA polymerase produces multiple amplicons. A billion-fold isothermic amplification can thus be achieved using two amplification primers.

A "target-binding sequence"0 of an amplification primer is the portion that determines target specificity because that portion is capable of annealing to the a target nucleic acid strand or its complementary strand. The complementary target sequence to which the target-binding sequence hybridizes is referred to as a primer-binding sequence. For primers or amplification methods that do not require additional functional sequences in the primer (e.g., PCR amplification), the primer sequence consists essentially of a target-binding sequence, whereas other methods (e.g., TMA or SDA) include additional specialized sequences adjacent to the target-binding sequence (e.g., an RNA polymerase promoter sequence adjacent to a target-binding sequence in a promoter-primer or a restriction endonuclease recognition sequence for an SDA primer). For example, in the preferred PSA-specific target-binding sequences shown in Table 1, SEQ IN NO:15 to SEQ ID NO:29 are amplification primers that do not include additional functional sequences, and SEQ ID NO:30 to SEQ ID NO:43 are T7 promoter-primers that include additional functional sequences (underlined) besides the target-binding sequences (not underlined); the underlined sequences are preferred T7 polymerase promoter sequences. It will be appreciated by those skilled in the art that all of the primer and probe sequences of the present invention may be synthesized using standard in vitro synthetic methods. Also, it will be appreciated that those skilled in the art could modify primer sequences disclosed herein using routine methods to add additional specialized sequences (e.g., promoter or restriction endonuclease recognition sequences) to make primers suitable for use in a variety of amplification methods. Similarly, promoter-primer sequences described herein can be modified by removing the promoter sequences to produce amplification primers that are essentially target-binding sequences, suitable for amplification procedures that do not use these additional functional sequences, such as PCR.

The PSA-specific sequences of the primers and probes of SEQ ID NO:1 to SEQ ID NO:43 and the hK2-specific sequences of primers of SEQ ID Nos. 46 and 47 were selected by aligning the known sequences of PSA exons with the known sequences of HSPSAR and human kallikrien exon sequences (HUMKAL2, HUMKAL2a, HUMKAL2b, HUMKAL2c, HUMKAL2d, HSKALLI, and HUMPSAA) using the an alignment algorithm using default parameters of the algorithm, such as, for example, the BLASTN algorithm available from the National Center for Biotechnology Information at the National Library of Medicine, or using the Multiple Alignment Construction and Analysis Workbench ("MACAW") algorithm as described in detail previously (Shuler et al., 1991, *Proteins* 9(3):180-190). After these sequences were aligned, regions of the PSA exon or hK2 region for which a primer or probe sequence was desired which contained the least amount of identity with the other sequences were identified. From those sequences, oligonucleotide sequences of the appropriate length and GC content for a primer or probe were selected and synthesized for tested. In some cases, the predicted secondary structure of the selected primer or probe sequence was determined by using an algorithm that calculates RNA secondary structure, as previously described in detail (Matzura and Wennborg, *Complete Applications in the Biosciences*,1996, Vol. 12, No. 3, pp 247-9). The primers of SEQ ID NO:48 and SEQ ID NO:49 and the probe of SEQ ID NO:50 for the human PSMA were similarly designed and selected. Although algorithms were used to aid in sequence alignment and predicting secondary structure, those skilled in the art could readily perform these steps manually.

By "target sequence" is meant the nucleotide base sequence of a nucleic acid strand, at least a portion of which is capable of being detected using a labeled oligonucleotide probe. Primers bind to a portion of a target sequence, which includes both complementary strands when the target sequence is a double-stranded nucleic acid.

By "equivalent RNA" is meant a ribonucleic acid having the same nucleotide base sequence as a deoxyribonucleic acid (DNA), with the appropriate U for T substitution(s). Similarly, an "equivalent DNA" is a DNA having the same nucleotide base sequence as an RNA but with the appropriate T for U substitution(s). It will be appreciated by those skilled in the art that the terms "nucleic acid" and "oligonucleotide" refer to molecular structures having either a DNA or RNA base sequence or a synthetic combination of DNA and RNA base sequences, including analogs thereof, which include "abasic" residues.

By "solid support" is meant a material that is essentially insoluble under the solvent and temperature conditions of the assay method, comprising free chemical groups available for joining an oligonucleotide or nucleic acid. Preferably, the solid support is covalently coupled to an oligonucleotide designed to directly or indirectly bind a target nucleic acid. When the target nucleic acid is an mRNA, the oligonucleotide attached to the solid support is preferably a poly-T sequence. A preferred solid support is a particle, such as a micron- or submicron-sized bead or sphere. A variety of solid support materials are contemplated, such as, for example, silica, polyacrylate, polyacrylamide, a metal, polystyrene, latex, nitrocellulose, polypropylene, nylon or combinations thereof. More preferably, the solid support is capable of being attracted to a location by means of a magnetic field, such as a solid support having a magnetite core. Particularly preferred supports are monodisperse magnetic spheres (i.e., uniform size ± about 5%).

By "detecting" an amplification product is meant any of a variety of methods for determining the presence of an amplified nucleic acid, such as, for example, hybridizing a labeled probe to a portion of the amplified product. A labeled probe is an oligonucleotide that specifically binds to another sequence and contains a detectable group which may be, for example, a fluorescent moiety, a chemiluminescent moiety, a radioisotope, biotin, avidin, enzyme, enzyme substrate, or other reactive group. Preferably a labeled probe includes an acridinium ester (AE) moiety that can be detected chemiluminescently under appropriate conditions (as described in U.S. Pat. No. 5,283,174). Other well know detection techniques include, for example, gel filtration, gel electrophoresis and visualization of the amplicons, and High Performance Liquid Chromatography (HPLC). The detecting step may either be qualitative or quantitative, although quantitative detection of PSA-specific or other prostate-associated genetic amplicons is preferred for determining the level of prostate-associated gene expression (e.g., PSA-specific mRNA) in a non-prostate sample, which indicates the degree of metastasis or recurrence of prostate and/or breast cancer.

Assays for purifying and detecting a target polynucleotide often involve capturing a target polynucleotide onto a solid support. The solid support retains the target polynucleotide during one or more washing steps of the target polynucleotide purification procedure. One hybridization sandwich technique for capturing and for detecting the presence of a target polynucleotide involves the capture of the target polynucleotide by a probe bound to a solid support and hybridization of a detection probe to the captured target polynucleotide (U.S. Pat. No. 4,486,539 to Ranki et al.). Detection probes not hybridized to the target polynucleotide are readily washed away from the solid support. Thus, remaining label is associated with the target polynucleotide initially present in the sample. Another method uses a mediator polynucleotide that hybridizes to both a target polynucleotide and to a polynucleotide fixed on a solid support such that the mediator polynucleotide joins the target polynucleotide to the solid support to produce a bound target (U.S. Pat. No. 4,751,177 to Stabinsky). A labeled probe can be hybridized to the bound target and unbound labeled probe can be washed away from the solid support.

Many methods for detecting mRNA, particularly those that include amplification, require extensive purification of RNA and/or mRNA prior to amplification and detection, often involving harsh chemicals such as guanidinium thiocyanate (Sambrook, J. et al., 1989, *Molecular Cloning, A Laboratory Manual*,2$^{nd}$ ed. (Cold Spring Harbor Laboratory Press, Cold Spring Harbor, N.Y.), pp. 7.37-7.57; Lin, L. et al., 1993, "Simple and Rapid Sample Preparation Methods for Whole Blood and Blood Plasma" in *Diagnostic Molecular Microbiology, Principles and Applications* (Persing, D. H. et al., Eds., American Society for Microbiology, Washington, D.C.), pp 605-616). One embodiment of the present invention uses a simple and rapid method for non-prostate biological sample preparation that results in RNA from which prostate-associated mRNA (e.g., PSA-specific mRNA) can be amplified and detected for detection of prostate and/or breast cancer cells in non-prostate tissue.

Non-prostate biological samples may be hematopoietic tissue such as peripheral blood or bone marrow, plasma, non-prostate biopsy tissue including lymph nodes, respiratory tissue or exudates, gastrointestinal tissue, urine, feces, semen or other body fluids or materials. The preferred sample preparation method requires a minimum of technical expertise and uses standard laboratory equipment and relatively low cost reagents to yield target mRNA suitable for amplification, while avoiding false positives that may result from potentially cross-reactive sequences found in chromosomal DNA. The preferred simplified sample preparation method eliminates extensive extraction and shearing of chromosomal DNA (to reduce viscosity), avoids use of potentially harmful reagents (e.g., guanidinium compounds, phenol or chloroform) and minimizes the number of steps, thus minimizing sample loss and increasing detection of low abundance mRNA species.

The methods invention includes a method of detecting or quantifying prostate-associated genetic markers, such as PSA-specific nucleic acids, particularly mRNA. The methods include contacting a non-prostate biological sample that potentially contains a prostate-associated genetic marker target sequence with a first primer or promoter-primer capable of specifically hybridizing to the target gene sequence (PSA, PSMA and/or hK2), and providing at least one nucleic acid polymerase activity, under nucleic acid amplification conditions to produce target-specific amplification products ("amplicons"). Preferably, the target-specific amplification products are a plurality of a nucleic acid strands comprising a region complementary to the specific target sequence and at least one probe binding site capable of hybridizing under hybridization conditions with a labeled oligonucleotide probe specific for the amplified target sequences, thereby forming a probe:target hybrid. The method also includes detecting the labeled probe:target hybrid as an indication of the presence of the prostate-associated genetic marker nucleic acid in the non-prostate biological sample. Preferred embodiments further include preparation of the target nucleic acid substrate from the biological sample using a relatively simple sample preparation procedure. The detecting step may further include one or more helper probes specific for a portion of the amplified target nucleic acid to enhance detection of the target in the assay. Although not wishing to be bound by the mechanism by which the helper probe(s) enhance detection, it is generally thought that helper probes hybridize to the amplified target sequences to remove secondary structure or otherwise enhance the capability of the other probes to bind to the detected sequence. Preferably, if the prostate-associated genetic marker target sequence is RNA, then the labeled oligonucleotide probe is of the same sense.

In one embodiment of the present method, only a promoter-primer is used in the amplifying step and the probe is targeted to a portion of the amplicon. When a single promoter-primer is employed with no primer of the opposite sense, the target RNA is detected using a probe of the same sense as the target RNA and capable of hybridizing with a base sequence region located within the amplified complementary nucleic acid (as previously described in detail in U.S. Pat. No. 5,554,516 to Kacian et al.).

In preferred embodiments of the present invention, selected primers specific for human PSA, PSMA and/or hK2 gene sequences are used in a transcription mediated amplification that uses both a promoter-primer and an amplification primer without promoter sequence, and the amplified products are detected with a probe capable of being detected in a homogeneous assay (see U.S. Pat. Nos. 5,480,784 and 5,399,491 to Kacian & Fultz; U.S. Pat. No. 5,554,516 to Kacian et al.; U.S. Pat. No. 5,283,174 to Arnold et al.; European Pat. App. No. EP 0709466). These general amplification and detection methods are well known in the art. The preferred amplification method produces an amplified nucleic acid or amplicon that is an RNA, and even more preferably produces predominantly amplified RNA that is complementary to the target sequence (i.e., the opposite sense as the target). Thus, if the target is mRNA, arbitrarily designated (+) sense strands, then the amplicons are preferably (−) sense strands. The probes for detecting such amplicons are any sequence capable of hybridizing specifically to an amplified sequence (i.e., are complementary to a portion of the amplicon). Using transcription-mediated amplification ("TMA") methods as described previously (U.S. Pat. Nos. 5,480,784 and 5,399,491), the promoter-primer is of the (−) sense the template target nucleic acid is of the (+) sense, and the produced amplicons are of the (−) sense.

This method is substantially isothermal and is preferable to prior art methods for detecting PSA-specific sequences because it does not require temperature cycling for nucleic acid amplification or nested primers for PSA-specific serial amplification. In particularly preferred embodiments of the present method, one of the two primers used in the amplification step is a T7 (− sense) promoter-primer that binds to the prostate-associated genetic marker mRNA and one of the two primers is a non-T7 (+ sense) primer that binds to the cDNA product produced from the activity of reverse transcriptase extending the T7 promoter-primer that uses the mRNA as a template. The T7 promoter-primer contains a T7 RNA polymerase recognition sequence at the 5' end of the target-binding sequence, whereas the non-T7 primer does not contain a T7 RNA polymerase recognition sequence and consists essentially of a target-binding sequence. Preferred promoter-primers have a length range having a lower limit of between about 35-45 nt and an upper limit between about 45-100 nt. Preferably, promoter-primers are about 40-70 nt long, and more preferably are about 45-55 nt long. Preferably, a T7 promoter sequence of a promoter-primer is about 25-30 nt long; particularly preferred T7 promoter sequences include SEQ ID NO:44 or SEQ ID NO:45. Preferred target-binding regions of a PSA-specific promoter-primer hybridize specifically to a human PSA gene exon sequence, preferably within any one of exons 3, 4 or 5. Primers used in transcription mediated amplification in conjunction with promoter primers consist essentially of target-binding sequences specific for human PSA, PSMA or hK2 gene sequences. Preferred PSA-specific bind to PSA sequences within an exon or spanning a splice junction of two exons, and more preferably have target-binding sequences specific for any one of exons 2, 3 or 4, or span the exon 2 and 3 splice junction of the human PSA gene. Primers preferably have a length within a range having a lower limit of about 15-20 nt and an upper limit within a range of about 25-100 nt, more preferably in a range of about 15-30 nt, and most preferably in a range of about 20-25 nt in length. As shown in Table 1, preferred PSA-specific primers have the sequences of SEQ ID NO:15 to SEQ ID NO:29 and preferred PSA-specific promoter-primers have the sequences of SEQ ID NO:30 to SEQ ID NO:43, where the promoter sequence is underlined and the target-binding sequence is not underlined.

One aspect of the present invention is a method of amplifying a PSA-specific target sequence in mRNA present in a sample taken from non-prostate tissue and detecting the amplified product as an measure of prostate or breast cancer cells present in non-prostate tissue, thus indicating the presence of breast cancer or metastasis of prostate cancer. Although a homogeneous chemiluminescent detection assay for detecting the nucleic acid probe is a preferred embodiment, those skilled in the art could readily use other labels and detection methods well known in the art, such as labels based on enzymes, enzyme substrates, fluorescent, luminescent, chemiluminescent and electrochemiluminescent molecules, radionuclides, and fluorescent atoms to detect a hybridized probe; the amplification product may be detected using standard methods such as by gel electrophoresis or filtration, increased light absorption, hyperchromatic shift, or HPLC. Preferred homogeneous assays have advantages over heterogeneous assays (i.e., those necessitating physical separation to differentiate signal of hybridized probe from signal due to unhybridized probe), but the homogeneous detection aspect is not critical to the present invention. Preferably a fluorescent or chemiluminescent label is incorporated into the probe, and more preferably the label is a chemiluminescent acridinium ester (AE).

Probes for use in the methods of the present invention may be targeted to any region of the amplicon to be detected, and preferably the probe is of the same sense as the target nucleic acid. For example, a PSA-specific probe may hybridize to either on intron or exon sequence, and preferably hybridizes to a sequence within a PSA gene exon (e.g., in exon 2, 3 or 4), or spanning an exon splice site (e.g., spanning the 3' end of exon 3 and the 5' end of exon 4), or within a PSA gene intron (e.g., within intron 3). Probe sequences may be within a range of about 5-100 nt long, and preferably are within about 10-50 nt long, more preferably about 20-25 nucleotides long. Preferred probe sequences include those having SEQ ID NO:1 to SEQ ID NO:14 (with their general location in the human PSA gene shown in Table 1) and SEQ ID NO:50. Preferably, the probes are AE-labeled and hybridize to the amplified RNA products of a TMA reaction.

The primers and probes of the present invention may be used in amplification and detection methods that use nucleic acid substrates isolated by any of a variety of well known methods. The target mRNA may be prepared by the following relatively simple procedure to yield mRNA suitable for use in TMA. In this procedure, cells in a biological sample (e.g., peripheral blood or bone marrow cells) were lysed by contacting the cell suspension with a lysing solution containing at least about 150 mM of a soluble salt, preferably a lithium halide salt, a chelating agent and a non-ionic detergent in an effective amount to lyse the cellular cytoplasmic membrane without causing substantial release of nuclear DNA or RNA. The cell suspension and lysing solution were mixed at a ratio of about 1:1 to 1:3, and the detergent concentration in the lysing solution was between about 0.5% to 1.5% (v/v). Any of a variety of known non-ionic detergents are effective in the lysing solution (e.g.,TRITON®-type, TWEEN®-type and NP-type); typically the lysing solution contained an octylphenoxy polyethoxyethanol detergent, preferably 1% TRITON® X-102. This procedure has been used primarily with biological samples that contain cell suspensions (e.g., blood and bone marrow), but it works equally well on other tissues if the cells are separated using standard mincing, screening and/or proteolysis methods to separate cells individually or into small clumps. After cell lysis, the released total RNA was stable, and may be stored at room temperature for at least 2 hr without significant RNA degradation without additional RNAse inhibitors. Total RNA may be used in amplification without further purification, or mRNA may be isolated using standard methods, generally dependent on affinity binding to the poly-A portion of mRNA.

Preferably mRNA isolation used capture particles consisting essentially of poly-dT oligonucleotides attached to insoluble particles that were added to the above-described lysis mixture, the poly-dT moieties annealed to the poly-A mRNA, and the particles were separated physically from the mixture. Generally, superparamagnetic particles were used and separated by applying a magnetic field to the outside of the container. Preferably, a suspension of about 300 µg of particles (in a standard phosphate buffered saline (PBS), pH 7.4, of 140 mM NaCl) having either $dT_{14}$ or $dT_{30}$ linked at a density of about 1 to 100 pmoles per mg (preferably 10-100 pmols/mg, more preferably 10-50 pmols/mg) were added to about 1 ml of lysis mixture. Any superparamagnetic particles may be used, although typically the particles were a magnetite core coated with latex or silica (e.g., commercially available from Serodyn or Dynal) to which poly-dT oligonucleotides were attached using standard procedures (Lund et al. *Nuc. Acids Res.*, 1988, 16:10861-10880). The lysis mixture containing the particles was gently mixed and incubated at about 22° C. to 42° C. for about 30 min, when a magnetic field was applied to the outside of the tube to separate the particles with attached mRNA from the mixture and the supernatant was removed. The particles were washed one or more times, generally three, using standard resuspension methods and magnetic separation as described above. Then, the particles were suspended in a buffer solution and used immediately in amplification or stored frozen.

A number of parameters may be varied without substantially affecting the sample preparation. For example, the number of particle washing steps may be varied and the particles may be separated from the supernatant by other means (e.g., filtration, precipitation, centrifugation). The solid support may have nucleic acid capture probes joined thereto that are complementary to the specific target sequence or any particle or solid support that non-specifically binds the target nucleic acid may be used (e.g., polycationic supports as described in U.S. Pat. No. 5,599,667 to Arnold et al.). For amplification, the isolated RNA was released from the capture particles using a standard low salt elution process or amplified while retained on the particles by using primers that bind to regions of the RNA not involved in base pairing with the poly-dT or in other interactions with the solid phase matrix. The exact volumes and proportions described above are not critical and may be varied so long as significant release of nuclear material does not occur. Vortex mixing is preferred for small scale preparations but other mixing procedures may be substituted. But it is important that samples derived from biological tissue be treated to prevent coagulation, and the ionic strength of the lysing solution be at least about 150 mM, preferably 150 mM to 1 M, because lower ionic strengths lead to nuclear material contamination (e.g., DNA) that increases viscosity and may interfere with amplification and/or detection steps to produce false positives. Lithium salts are preferred in the lysing solution tor prevent RNA degradation, although other soluble salts (e.g., NaCl) combined with one or more known RNAse inhibitors would be equally effective.

Table 2 lists preferred combinations of primers and probes used for amplification and detection of PSA, PSMA and hK2 genetic markers, with or without helper probe(s), using TMA essentially as described previously in U.S. Pat. Nos.5, 399,491, 5,480,784, and 5,554,516, and detection in a homogeneous protection assay, essentially as described previously in U.S. Pat. No. 5,283,174. Each row represents a preferred combination. Of these, particularly preferred combinations for amplifying and detecting PSA mRNA are indicated with an asterisk (*) in each box of the row in Table 2. The last two entries in Table 2 are primers and probes for amplifying and detecting specifically hK2 target (SEQ ID NOS 46, 47 and 1) and PSMA target (SEQ ID NOS 48, 49 and 50).

Nucleic acids from a variety of biological samples have been used in testing the methods of prostate-associated marker mRNA amplification and detection with the primers and probes described herein, including in vitro transcripts of a PSA cDNA, whole blood spiked with in vitro transcripts of a PSA cDNA, total RNA isolated from a prostate cancer cell line (LNCaP cells, Horoszewicz J. S. et al., 1983, Cancer Res. 43: 1809-1818; ATCC No. CRL-10995), whole blood spiked with LNCaP cells, peripheral blood, breast tissue cells, lung cells, poly-A RNA isolated and tested individually from prostate cancer cells, lymph nodes, breast tissue cells, kidney cells, small intestine tissue cells and white blood cell genomic DNA. Total RNA (from lung, mammary gland and prostate) and poly-A RNA (from kidney, liver, lymph node, mammary gland, small intestine and prostate) were prepared using standard methods (derived from the method of Chirgwin et al., 1979, Biochem.18:5294, with poly-A RNA selected using oligo(dT) cellulose; commercially available from Clontech Laboratories, Inc., Palo Alto, Calif.). Total RNA and poly-A RNA were prepared from peripheral blood from normal human donors using substantially the same methods.

In vitro transcripts of a PSA cDNA were prepared using a PSA cDNA clone (obtained from the ATCC, Accession No.106527) present in a vector (pBluscript SK-; Adams et al., 1985, Nature 377(3): 174) or the PSA cDNA fragment of about 1.2 kb was subcloned into another vector (pSP64 poly(A) vector) for use in preparing in vitro transcripts. The plasmid DNA was prepared and purified using standard methods, linearized by enzymatic digestion at a point 3' of the cDNA insert, and transcribed using an RNA polymerase. Transcripts were prepared using standard methods and reagents (supplied in an AMPLISCRIBE Translation Kit, from Epicenter Technologies, Corp., Madison, Wis.).

TABLE 2

Preferred Combinations of Primers and Probes (SEQ ID NOs)

| Non-T7 primer | T7 promoter-primer | Probe | Helper Primer(s) |
|---|---|---|---|
| 15 | 30 | 1 | NONE |
| 17* | 30* | 1* | NONE |
| 18* | 30* | 1* | NONE |
| 18 | 35 | 1 | NONE |
| 18 | 30 | 4 | NONE |
| 18 | 30 | 5 | NONE |
| 18 | 30 | 6 | NONE |
| 16 | 31 | 2 | NONE |
| 16 | 31 | 3 | NONE |
| 16 | 33 | 2 | NONE |
| 16 | 33 | 3 | NONE |
| 16* | 32* | 2* | NONE |
| 16 | 32 | 3 | NONE |
| 16 | 34 | 2 | NONE |
| 16 | 34 | 3 | NONE |
| 20* | 37* | 8* | NONE |
| 20 | 38 | 8 | NONE |
| 21 | 37 | 8 | NONE |
| 21 | 38 | 8 | NONE |
| 21* | 40* | 14* | NONE |
| 21 | 37 | 14 | NONE |
| 21* | 41* | 14* | NONE |
| 21 | 40 | 8 | NONE |
| 21 | 41 | 8 | NONE |
| 21 | 41 | 8 | 27 |
| 21* | 41* | 8* | 27 & 28* |
| 26* | 40* | 8* | 27 & 28* |
| 26* | 37* | 8* | 27 & 28* |
| 26* | 41* | 8* | 27 & 28* |
| 26 | 43 | 8 | 27 & 28 |
| 26 | 38 | 8 | 27 & 28 |
| 46 | 47 | 1 | NONE |
| 48 | 49 | 50 | NONE |

Unless mentioned otherwise, the techniques employed or contemplated herein are standard methodologies well known to one of ordinary skill in the art. The examples of embodiments that follow are provided for illustration only.

EXAMPLE 1

Lysis of Biological Samples and Isolation of mRNA

About 250 µl of uncoagulated peripheral blood or bone marrow was added to about 750 µl of the lysing solution. The proportions of each of these two components is not critical, and generally a 1:1 ratio to 1:3 ratio of the components is capable of lysing the samples. The lysing solution used most commonly consisted of 50 mM HEPES (pH 7.5),1 M LiCl,5 mM EDTA, and 1% TRITON®X-102. By "uncoagulated" is meant that the blood or bone marrow was treated upon collection with about 2 mM to about 20 mM EDTA, or an effective amount of heparin or similar anticoagulant known in the art. To this mixture, a suspension of about 300 µg of superparamagnetic particles (in PBS solution, pH 7.4, containing 140 mM NaCl) having either $dT_{14}$ or $dT_{30}$ linked at a density of about 10 to 50 pmoles of poly dT per mg of particles was added. The lysis mixture containing the poly-dt particles was gently mixed by vortexing and incubated at between about 22° C. to 42° C. for about 30 min. The particles with attached mRNA were separated from the mixture by applying a magnetic field to the outside of the tube and removing the supernatant. The particles were washed one to three times by resuspending them in about 1 ml of a wash solution (50 mM HEPES, pH 7.5, 5 mM EDTA,150 mM NaCl and 0.1% (w/v) sodium dodecyl sulfate (SDS)) with mixing by vortexing for about 3 to 5 seconds to suspend the beads, which were separated from the supernatant as described above, and the supernatant wash was discarded. Following washing, the particles were suspended in 250 µl of a buffer (10 mM HEPES, pH 7.5, 1 mM EDTA) and either stored at −30° C. for later use or used immediately. For use in amplification procedures, the particles with attached RNA were used directly or, occasionally, the attached RNA was released from the capture particles using a standard elution procedures (e.g., with heat). The presence of solid particles did not impair amplification and the simplicity of using the particles with attached RNA was preferred to an additional RNA isolation step.

EXAMPLE 2

Amplification and Detection of PSA-Specific mRNA

To initially test the relative efficiency of different combinations of primers and promoter-primers in transcription mediated amplification of known PSA sequences, individual combinations of a non-T7(+) primer and a T7(−) promoter-primer were used to amplify an in vitro transcript (as described above) of PSA gene sequences. Following amplification, the amplification products were detected in a homogeneous protection assay essentially as described in U.S. Pat. No. 5,283,174, to Arnold et al., using a single probe labeled with acridinium ester, in which the chemiluminescent signal is detected as relative light units ("RLU"). All experimental samples were tested in triplicate, and the mean RLU of the three tests was calculated. For these experiments, the promoter-primer and the probe were the same in all reactions, but the non-T7 primers were varied. The T7 promoter-primer (SEQ ID NO:30) is specific for PSA exon 4, the primers are specific for PSA exon 3 (SEQ ID NO:15, SEQ ID NO:17 and SEQ ID NO:18), and the probe is specific for PSA exon 3 (SEQ ID NO:1).

Briefly, 50 μl of a solution containing different numbers of in vitro transcripts ($10^3$, $10^4$, or $10^5$ molecules, or a negative control containing no transcripts) was added to a tube containing 25 μl of an amplification reagent containing 160 mM Tris-HCl (pH 7.5),100 mM MgCl$_2$ 70 mM KCl,20% (w/v) polyvinylpyrrolidone,16 mM each of the four ribonucleoside triphosphates ATP, GTP, CTP, and UTP, 4 mM each of the four deoxyribonucleoside triphosphates dATP, dGTP, dCTP, and dTTP, 400 nM (15 pmoles). In the three combinations tested in this example, the T7 promoter-primer at 15 pmols/reaction (equivalent to about 400 nM) had the sequence of SEQ ID NO:30, and the non-T7 primer at 400 nM (15 pmoles) had the sequence of SEQ ID NO:15, SEQ ID NO:17, or SEQ ID NO:18. Each reaction was incubated at 60° C. for 10 min, although any temperature capable of melting intramolecular base pairing in the target nucleic acid is suitable (e.g., between about 60° C. and 70° C., more preferably between about 65° C. and about 67° C.). Then, each reaction was incubated at about 42° C. for 5 min, after which an enzyme reagent (25 μl containing 2000 units of recombinant MMLV reverse transcriptase, 2000 units recombinant T7 RNA polymerase,8 mM HEPES (pH 7.5), 50 mM N-acetyl-L-cysteine, 0.04 mM zinc acetate, 80 mM trehalose, 140 mM Tris-HCl (pH 8.0), 70 mM KCl,1 mM EDTA,0.01% (w/v) phenol red, 10% (v/v) TRITON® X-102 and 20% (v/v) glycerol) was added and the reaction was gently mixed and incubated for about 1 hr at 42° C. This amplification method produced amplified RNA of a sense opposite to that of the target RNA.

Amplified RNA was detected using 100 μl of a probe reagent containing 100 mM lithium succinate (pH 4.7), 1.2 M LiCl, 15 mM aldrithiol-2, 2% (w/v) lithium lauryl sulfate (LLS), 20 mM EDTA, 20 mM ethylene glycol-bis-(β-amino ethyl ether) N,N,N',N'-tetracetic acid (EGTA),3% ethanol, and 7.5 nM of a hybridization probe having SEQ ID NO:1, labeled with a chemiluminescent acridinium ester (AE) linked via non-nucleotide linkers using methods essentially a described in U.S. Pat. No. 5,585,481 to Arnold et al. The detection solution was added to the reaction and incubated at 60° C. for 30 min to permit hybridization of the probe to the amplified target.

The probe (SEQ ID NO:1) was detected in a homogeneous protection assay (HPA) which included the following steps. To hydrolyze the AE label on unbound probe,300 μl of an alkaline solution (600 mM sodium borate, pH 8.5, and 1% (v/v) TRITON® X-100) was added to the mixture described above. The AE label on hybridized probe is protected from hydrolysis by its association with a double helix, whereas the AE label on unhybridized probe is not protected from hydrolysis, making unhybridized probe undetectable. The solution was incubated at 60° C. for 10 min, cooled at room temperature for 5 min, and mixed with 200 μl of a solution containing 30 mM hydrogen peroxide and 1 mM nitric acid, followed immediately by addition of 200 μl of a solution containing 1 M NaOH and 2% (w/v) ZWITTERGENT® 3-14. Chemiluminescence was detected using a luminometer (e.g., LEADER® 50), with the output measured in relative light units ("RLU").

The results of these tests are shown in Table 3, in which the mean number of RLU detected for each of three tests for each combination of primer and promoter-primer is presented. Each combination of primer and promoter-primer was tested using no PSA transcripts (negative control) and individually with $10^3$, $10^4$, or $10^5$ transcripts.

TABLE 3

PSA Target Amplification and Detection with Different Combinations of Primers

| Non-T7 Primer SEQ ID NO (PSA exon) | T7 Promoter-primer SEQ ID NO (PSA exon) | PSA Transcripts (molecules/reaction) | Mean Signal (RLU) |
|---|---|---|---|
| 15 (exon 3) | 30 (exon 4) | $10^5$ | 504,097 |
| 15 | 30 | $10^4$ | 56,481 |
| 15 | 30 | $10^3$ | 5,528 |
| 15 | 30 | 0 | 950 |
| 17 (exon 3) | 30 (exon 4) | $10^5$ | 31,656 |
| 17 | 30 | $10^4$ | 3,409 |
| 17 | 30 | $10^3$ | 1,217 |
| 17 | 30 | 0 | 983 |
| 18 (exon 3) | 30 (exon 4) | $10^5$ | 1,490,310 |
| 18 | 30 | $10^4$ | 1,451,391 |
| 18 | 30 | $10^3$ | 505,344 |
| 18 | 30 | 0 | 901 |

The results shown in Table 3 show that the three combinations of primers and promoter-primers tested in this example gave varying levels of amplification, all detected with the same probe, and all provided a signal above background when $10^3$ copies of the target RNA were included in the assay. Of these three combinations, the combination of SEQ ID NO:18 and SEQ ID NO:30 gave the best results, and the system became saturated for detection when $10^4$ copies of the target RNA were included in the assay.

EXAMPLE 3

Amplification and Detection of PSA mRNA in Total and Poly-A RNA from Prostate Tissue In this example, a number of combinations of primer, promoter-primer and probe were used to amplify and detect PSA-specific mRNA contained within a sample of total RNA prepared from prostate tissue as described above.

The transcription mediated amplification and chemiluminescence detection steps were performed substantially as described in Example 2. Initially, to determine the sensitivity of the assay, total RNA was used over a range of 1 pg to 10 ng, representing the RNA content of different numbers of prostate cells. That is, the total RNA in the tested samples was equivalent to a calculated numbers of cells as follows: 1 pg is equivalent to less than 1 cell (about 0.1 cell),10 pg is equivalent to about 1 cell, 100 pg is equivalent to about 10 cells,1,000 pg (1 ng) is equivalent to about 100 cells, and 10,000 pg (10 ng) is equivalent to about 100 cells. In some experiments, the total range of RNA concentrations were not tested. A negative control (background) of no added RNA was included in all tests, and all tests were performed in triplicate with the mean RLU reported in Table 4. Table 4 shows the results for a number of combinations of non-T7 (+) primers and T7(−) promoter-primers used in amplification, and detected with a number of AE-labeled probes.

TABLE 4

PSA Target Amplification and
Detection with Different Combinations of Primers and Probes

| Non-T7 Primer SEQ ID NO (PSA Exon) | T7 promoter-primer SEQ ID NO (PSA Exon) | Probe SEQ ID NO (PSA Exon) | Total RNA Added | Mean RLU |
|---|---|---|---|---|
| 18 (exon 3) | 30 (exon 4) | 1 (exon 3) | 10 ng | 1,592,092 |
| 18 | 30 | 1 | 1 ng | 1,395,934 |
| 18 | 30 | 1 | 100 pg | 966,851 |
| 18 | 30 | 1 | 10 pg | 352,476 |
| 18 | 30 | 1 | 1 pg | 50,249 |
| 18 | 30 | 1 | 0 | 520 |
| 20 (exon 2) | 37 (exon 3) | 8 (exon 2) | 1 ng | 2,490,049 |
| 20 | 37 | 8 | 0 | 4,780 |
| 21 (exon 2) | 40 (exon 3) | 14 (exon 2) | 10 pg | 1,061,753 |
| 21 | 40 | 14 | 1 pg | 130,779 |
| 21 | 40 | 14 | 0.1 pg | 41,248 |
| 21 | 40 | 14 | 0 | 32,866 |
| 21 (exon 2) | 37 (exon 3) | 14 (exon 2) | 10 pg | 108,811 |
| 21 | 37 | 14 | 1 pg | 52,603 |
| 21 | 37 | 14 | 0.1 pg | 34,963 |
| 21 | 37 | 14 | 0 | 37,440 |
| 21 (exon 2) | 41 (exon 3) | 14 (exon 2) | 10 pg | 3,188,114 |
| 21 | 41 | 14 | 1 pg | 237,928 |
| 21 | 41 | 14 | 0.1 pg | 60,460 |
| 21 | 41 | 14 | 0 | 37,140 |
| 21 (exon 2) | 40 (exon 3) | 8 (exon 2) | 10 pg | 107,787 |
| 21 | 40 | 8 | 1 pg | 36,444 |
| 21 | 40 | 8 | 0.1 pg | 8,735 |
| 21 | 40 | 8 | 0 | 5,953 |
| 21 (exon 2) | 37 (exon 3) | 8 (exon 2) | 10 pg | 67,169 |
| 21 | 37 | 8 | 1 pg | 13,555 |
| 21 | 37 | 8 | 0.1 pg | 7,833 |
| 21 | 37 | 8 | 0 | 5,037 |
| 21 (exon 2) | 41 (exon 3) | 8 (exon 2) | 10 pg | 261,249 |
| 21 | 41 | 8 | 1 pg | 44,013 |
| 21 | 41 | 8 | 0.1 pg | 6,308 |
| 21 | 41 | 8 | 0 | 5,242 |

As can be seen from the results shown in Table 4, all of the combinations of primers, promoter-primers and probes detected PSA mRNA in the total RNA sample added to the reaction compared to the background signal for each combination, where no RNA was added. Furthermore, a signal significantly greater than background was generally detected when as little as 1 pg of RNA was added (equivalent to about the amount calculated to be present in 0.1 cell).

These results were confirmed in separate tests using poly-A RNA isolated from prostate tissue. The prostate poly-A RNA was isolated using poly-dT hybridization in which the poly-dT oligonucleotides were about $dT_{14}$ to $dT_{30}$ in length and covalently linked to magnetic particles; the purification steps used (magnetic separation and washing) were substantially as described in Example 1. It was expected that total prostate RNA would contain about 5% PSA-specific mRNA, and the amount of poly-A RNA (i.e., purified mRNA) added to the amplification and detection samples was reduced accordingly. In one set of tests, poly-A RNA from prostate tissue was added to triplicate tubes at 5 pg or 0.5 pg per reaction, which were amplified and detected using the combination of SEQ ID NO:18 and SEQ ID NO:30 as primers, and SEQ ID NO:1 as probe, substantially as described for the results presented in Table 4. For 5 pg of prostate mRNA, the mean RLU detected were 1,404,286 and for 0.5 pg the mean RLU detected were 392,558. These results show that further purification of the PSA-specific target, although not necessary for amplification and detection, produces a detectable signal with as little as 0.5 pg of mRNA.

To determine whether helper primers added to an amplification reaction would increase the signal detected, a series of amplification and detection experiments were performed as described in the next example.

EXAMPLE 4

Amplification and Detection of PSA-specific Target with Helper Probes

This example demonstrates that addition of one or more helper probes may increase the signal detected, allowing detection of PSA-specific sequences present in less than 0.1 pg of total RNA isolated from prostate tissue using the preferred amplification and detection system. In these tests, amplification was performed substantially as described in Examples 2 and 3, except that about 100 pmol of helper probe oligonucleotides were added to the amplification reaction along with the AE-labeled probe using in the detection step. Amplification then proceeded as described above, followed by detection of chemiluminescence as described above. The PSA-specific target was provided in total RNA isolated from prostate tissue as described in Example 3, tested at concentrations ranging from 0.016 pg to 10 pg. The helper probes in these experiments were SEQ ID NO:27 (in PSA exon 2) and SEQ ID NO:28 (spanning the joining point of PSA exons 2 and 3). The results of these tests are shown in Table 5, with the signal representing the mean of triplicate samples for each RNA concentration tested.

TABLE 5

Amplification with Helper Probes and Detection
of PSA-specific Sequences

| Non-T7 Primer SEQ ID NO (PSA Exon) | T7 promoter-primer SEQ ID NO (PSA Exon) | Probe SEQ ID NO (PSA Exon) | RNA Added Per Reaction (pg) | Mean RLU |
|---|---|---|---|---|
| 21 (exon 2) | 41 (exon 3) | 8 (exon 2) | 10 | 7,539,550 |
| 21 | 41 | 8 | 1 | 1,065,253 |
| 21 | 41 | 8 | 0.5 | 422,459 |
| 21 | 41 | 8 | 0.25 | 174,277 |
| 21 | 41 | 8 | 0.125 | 126,543 |
| 21 | 41 | 8 | 0.062 | 39,283 |
| 21 | 41 | 8 | 0.031 | 24,898 |
| 21 | 41 | 8 | 0.016 | 5,504 |
| 21 | 41 | 8 | 0.000 | 3,645 |

To show that the amplification and detection system was specific for PSA mRNA detection, amplification and detection reactions were performed on total RNA isolated from prostate tissue (obtained from Clonetech, Palo Alto, Calif.) compared to total RNA isolated from white blood cells ("WBC") obtained from peripheral blood of normal donors. Helper probes (SEQ ID NO:27 and SEQ ID NO:28) were included in all of these amplification reactions at a concentration of about 100 pmol and four different combinations of non-T7 primer, T7 promoter-primer and probe. In these tests, the prostate total RNA was used at 10 pg or 1 pg per reaction, whereas at least 10,000-fold more WBC total RNA was used for comparison (1 μg or 100 ng per reaction). For each set of reactions, a negative control with no added RNA was included, and all reactions were tested in triplicate, with the results presented as the mean of the three reactions (Mean RLU). The results are presented in Table 6.

TABLE 6

Specificity of Amplification with Helper Probes and Detection of PSA-specific Sequences

| Non-T7 Primer SEQ ID NO (PSA Exon) | T7 promoter-primer SEQ ID NO (PSA Exon) | Probe SEQ ID NO (PSA Exon) | Total RNA Added Per Reaction & Source | Mean RLU |
|---|---|---|---|---|
| 21 (exon 2) | 41 (exon 3) | 8 (exon 2) | 10 pg - Prostate | 5,217,830 |
| 21 | 41 | 8 | 1 pg - Prostate | 441,752 |
| 21 | 41 | 8 | 1 μg - WBC | 4,667 |
| 21 | 41 | 8 | 100 ng - WBC | 16,136 |
| 21 | 41 | 8 | 0 | 2,552 |
| 26 (exon 2) | 40 (exon 3) | 8 (exon 2) | 10 pg - Prostate | 9,085,005 |
| 26 | 40 | 8 | 1 pg - Prostate | 2,708,971 |
| 26 | 40 | 8 | 1 μg - WBC | 7,417 |
| 26 | 40 | 8 | 100 ng - WBC | 6,124 |
| 26 | 40 | 8 | 0 | 2,641 |
| 26 (exon 2) | 37 (exon 3) | 8 (exon 2) | 10 pg - Prostate | 3,709,715 |
| 26 | 37 | 8 | 1 pg - Prostate | 462,262 |
| 26 | 37 | 8 | 1 μg - WBC | 18,889 |
| 26 | 37 | 8 | 100 ng - WBC | 5,122 |
| 26 | 37 | 8 | 0 | 2,592 |
| 26 (exon 2) | 41 (exon 3) | 8 (exon 2) | 10 pg - Prostate | 2,710,422 |
| 26 | 41 | 8 | 1 pg - Prostate | 439,147 |
| 26 | 41 | 8 | 1 μg - WBC | 8,409 |
| 26 | 41 | 8 | 100 ng - WBC | 4,738 |
| 26 | 41 | 8 | 0 | 2,676 |

As can be seen from the results shown in Table 6, each of the four combinations of primers and probes tests specifically amplified and detected PSA-specific target RNA in prostate total RNA. In contrast, the results were essentially negative for the samples under the same conditions that included WBC total RNA from a normal donor which would not be expected to contain PSA-specific target mRNA. That is, despite the use of 1 0,000-fold to 1,000,000-fold more WBC total RNA in the reactions compared to prostate total RNA, no false positives were observed (i.e., none gave results equivalent to those obtained with 1 pg of prostate RNA). The relatively high mean RLU (16,136 Mean RLU) presented in Table 6 for the tests using 100 ng of WBC total RNA and the combination of SEQ ID NO:21, SEQ ID NO:41 and SEQ ID NO:8 resulted from a single tube in which 43,485 RLU were detected, compared to the other two tubes in the set (2,458 and 2,464 RLU) which were essentially the same as the negative control; the single high result may have been due to contamination or operator error.

Figure 5:
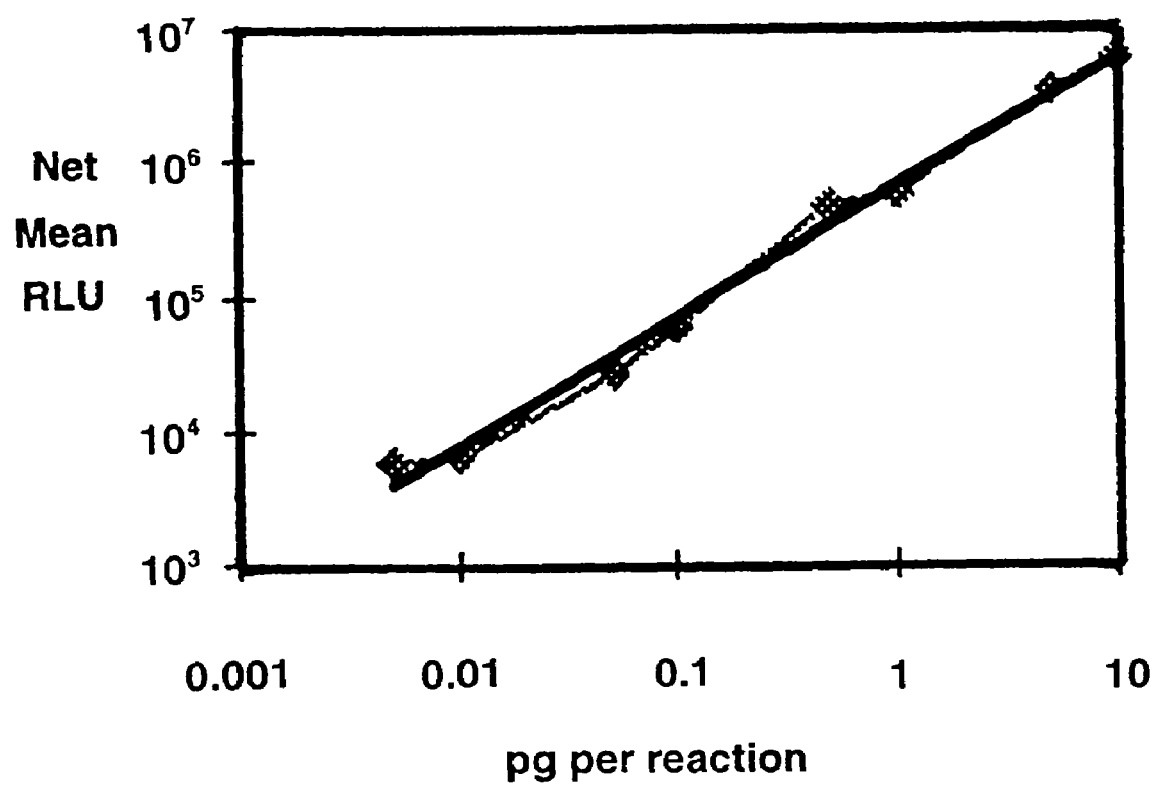
FIG. 5 is a diagram showing the linearity of PSA-specific target amplification and detection of chemiluminescence (Net Mean RLU) in assays containing 10, 5, 1, 0.5, 0.1, 0.05, 0.01 or 0.005 pg of prostate total RNA per reaction, in which the experimental results are shown as a dotted line and dotted symbols and the calculated linear regression line is solid.

In separate tests, the linearity of detection of PSA-specific target sequence was measured in an amplification and detection assay in which the combination of non-T7(+) primer of SEQ ID NO:26, T7 promoter primer of SEQ ID NO:40 and probe of SEQ ID NO:8 was used with prostate total RNA over a range of 10 pg to 0.001 pg per reaction (i.e., using 10, 5, 1, 0.5, 0.1, 0.05, 0.01 or 0.005 pg per reaction). The test aliquots were prepared from the 10 pg aliquot by diluting 1:2 and 1:10 to obtain a 5 pg and 1 pg aliquots; the 5 pg aliquot was then serially diluted 1:10 to obtain the 0.5, 0.05 and 0.005 pg aliquots and the 1 pg aliquot was similarly diluted to obtain the 0.1 and 0.01 pg aliquots. All assays were performed in triplicate, and the negative control contained no prostate total RNA in the reaction. The results of these assays are shown graphically in FIG. 5, in which both the X-axis and the Y-axis are logarithmic scales; by "net mean RLU" is meant that the mean of the negative control results was subtracted from the mean RLU of the experimental samples. Referring to FIG. 5, the experimental results are shown with dotted symbols and a dotted line, and the calculated linear regression of these results in shown as a solid line, with a fit of $R^2$ equal to 0.9776. When results within a series of 10-fold serial dilutions of total RNA were similarly graphed and $R^2$ values were calculated, within the 10, 1, 0.1 and 0.01 pg group the $R^2$ value was 0.9997 and within the 5, 0.5, 0.05 and 0.005 pg group the $R^2$ value was 0.9879. These results show that the amplification and detection system described herein is quantitative for detection of PSA-specific target nucleic acids.

EXAMPLE 5

Amplification and Detection of PSA Target Sequences in Denatured Genomic DNA

To show that the negative results obtained in Example 4 with RNA isolated from peripheral WBC were due to the lack of PSA gene expression in WBC, amplification and chemiluminescent detection assays were performed using denatured and undenatured genomic DNA obtained from peripheral WBC. The genomic DNA is expected to contain normal PSA gene sequences, which would be inaccessible to primers for amplification or probe for detection in its undenatured state. In these experiments the non-T7 (+) primer was SEQ ID NO:18, the T7 promoter-primer was SEQ ID NO:30 and the AE-labeled probe was SEQ ID NO:30. The positive control was PSA gene in vitro transcripts prepared substantially as in Example 2 and used as 100 copies per reaction, 10 copies per reaction and 1 copy per reaction. The negative control was a reaction run without addition of nucleic acid target (DNA or RNA). The WBC genomic DNA was isolated using standard DNA isolation procedures, with shearing to decrease viscosity in solution (Sambrook et al. *Molecular Cloning, A Laboratory Manual* (2nd Ed.), Vol. 1-3, Cold Spring Harbor Laboratory, Cold Spring Harbor, N.Y., 1989), and used with or without prior denaturation at about 5 μg, 0.5 μg and 0.05 μg per reaction. The DNA was denatured by heating to 95° C. for about 10 min and then cooled immediately. Amplification and detection assays were performed substantially as described in Examples 2 and 3, and the results of triplicate tests for each sample are presented as mean RLU in Table 7.

TABLE 7

Amplification and Detection of PSA Target Sequence in WBC Denatured Genomic DNA

| Nucleic Acid Sample | Nucleic Acid Per Reaction | Mean RLU |
|---|---|---|
| WBC Undenatured DNA | 5 μg | 18,234 |
| WBC Undenatured DNA | 0.5 μg | 21,429 |
| WBC Denatured DNA | 5 μg | 1,391,494 |
| WBC Denatured DNA | 0.5 μg | 293,522 |
| PSA In Vitro Transcripts | 100 copies | 1,457,098 |

TABLE 7-continued

Amplification and Detection
of PSA Target Sequence in WBC Denatured Genomic DNA

| Nucleic Acid Sample | Nucleic Acid Per Reaction | Mean RLU |
|---|---|---|
| PSA In Vitro Transcripts | 10 copies | 448,603 |
| PSA In Vitro Transcripts | 1 copy | 1,028 |
| None | None | 1,068 |

The results shown in Table 7 show that the WBC genomic DNA contained PSA gene sequences which were amplified and detected when the DNA was denatured, with a decrease in signal consistent to the decrease in amount of target added to the reaction. In contrast, WBC undenatured DNA gave a relatively high background that was essentially the same at both concentrations tested, but was at least 10-fold less than the signal detected with 0.5 μg WBC denatured DNA under the same conditions.

EXAMPLE 6

Amplification of Prostate Poly-A RNA and PSA In Vitro Transcripts

This example compares amplification and detection results using a preferred combination of primers and probe, for which the target nucleic acid was either poly-A RNA isolated from prostate tissue or in vitro transcripts of a PSA cDNA sequence. The prostate poly-A RNA was isolated using hybridization to poly-dT oligomers immobilized to a solid support, substantially as described in Examples 1 and 3, and the in vitro transcripts were prepared substantially as described in Example 2. The amplification and detection methods were performed substantially as described in Examples 2-4, using as a non-T7(+) primer an oligonucleotide having SEQ ID NO:16, as a T7(−) promoter-primer an oligonucleotide having SEQ ID NO:32 and as a probe an oligonucleotide having SEQ ID NO:2, labeled with AE. The target sequences were added to the amplification reactions, which were performed in triplicate for each combination, at a calculated concentration of 10,000 copies of in vitro transcript per tube or 0.875 ng of poly-A-containing prostate RNA per tube, or no added RNA in the negative control tubes. The mean results were: 4,022 RLU for the negative control, 8,858 RLU for the in vitro transcript samples, and 1,791,197 for the poly-A RNA samples. That is, although the detected chemiluminescence in these tests was relatively low compared to other examples, the combination of SEQ ID NO:16, SEQ ID NO:32 and SEQ ID NO:2 was capable of amplifying and detecting PSA-specific target nucleic acid in the two positive samples (PSA in vitro transcripts and prostate mRNA) compared to the negative control.

EXAMPLE 7

Amplification and Detection of PSA-specific Target in Clinical Peripheral Blood Samples In this example, clinical samples of peripheral blood were tested from individuals suspected of having either benign prostate hyperplasia or prostate cancer. Peripheral blood samples were collected shortly before prostate surgery (pre-surgery) and soon after surgical removal of the prostate gland (post-surgery). For comparison, known numbers of cells of a prostate cancer cell line (LNCaP cells; ATCC No. CRLI-1 0995) or PSA-specific in vitro transcripts (as described in Example 2) were mixed with peripheral blood obtained from a normal individual. The clinical or control blood samples were lysed and the mRNA was isolated using the system of poly-dT oligomers attached to magnetic particles substantially as described in Example 1. About 1.2 ml of lysate of clinical samples was used per assay; and about 1.0 ml of lysate for LNCaP cells was used for comparison. The amplification and detection methods were performed substantially as described in Examples 2-4, using as a non-T7(+) primer an oligonucleotide having SEQ ID NO:18, as a T7(−) promoter-primer an oligonucleotide having SEQ ID NO:30 and as a probe an oligonucleotide having SEQ ID NO:1, labeled with AE. The target sequences were added to the amplification reactions, which were performed in triplicate for each sample, at: (1) about 50 to 100 ng of total RNA, equivalent to about 2.5 to 5 ng of mRNA per reaction for each clinical sample, (2) a calculated concentration of 2,000 or 200 or 20 copies of in vitro transcript per reaction, and (3) the calculated equivalent of about 10 cells,1 cell or 0.1 LNCaP cell per reaction. Negative control reactions contained no added RNA. The mean RLU results for the triplicate samples for each set of reactions, or mean RLU of nine reactions for the negative controls, are presented in Table 8.

TABLE 8

Amplification and Detection of
PSA-specific Target mRNA in Peripheral Blood Samples

| Sample | RNA Target Amount or Equivalent per Reaction | Mean RLU Detected |
|---|---|---|
| Blood + PSA In Vitro Transcripts | 2,000 copies | 1,243,606 |
| Blood + PSA In Vitro Transcripts | 200 copies | 190,850 |
| Blood + PSA In Vitro Transcripts | 20 copies | 25,877 |
| Clinical Sample 1, pre-surgery | 2.5-5.0 ng poly A RNA | 53,053 |
| Clinical Sample 1, post-surgery | 2.5-5.0 ng poly A RNA | 58,858 |
| Clinical Sample 2, pre-surgery | 2.5-5.0 ng poly A RNA | 1,436 |
| Clinical Sample 2, post-surgery | 2.5-5.0 ng poly A RNA | 1,346 |
| Clinical Sample 3, pre-surgery | 2.5-5.0 ng poly A RNA | 2,354 |
| Clinical Sample 3, post-surgery | 2.5-5.0 ng poly A RNA | 1,447 |
| Clinical Sample 4, pre-surgery | 2.5-5.0 ng poly A RNA | 1,286 |
| Clinical Sample 4, post-surgery | 2.5-5.0 ng poly A RNA | 1,329 |
| Blood + LNCaP cells | ≈10 LNCaP cells | 1,087,426 |
| Blood + LNCaP cells | ≈1.0 LNCaP cell | 200,122 |
| Blood + LNCaP cells | ≈0.1 LNCaP cell | 21,807 |
| Normal Blood (Negative Control) | None | 1,330 |

Based on these results, it is clear that the primers and probe are capable of detecting PSA-specific target RNA less than the equivalent of one cancer cell in a volume of about 1.0 ml peripheral blood as detected in the sample containing the equivalent of one LNCaP cell. Based on the blood samples containing in vitro PSA gene transcripts, it is clear that the assay is capable of detecting as little as 20 copies of transcript in a blood sample. By comparison with the results obtained in these positive controls and the negative controls to which no target RNA were added, the RLU detected in Clinical Sample No. 1 shows the presence of PSA-specific target in the peripheral blood, indicative of prostate cancer in the patient which is shedding cells into the blood and may have metastasized. In contrast, Clinical Sample Nos. 2 to 4 did not contain detectable PSA-specific nucleic acid in this assay, indicative of benign prostate hyperplasia ("BPH") instead of prostate cancer in those patients. For all of the clinical samples tested, the levels of RLU detected in pre-surgery and post-surgery samples obtained from individual patients were not significantly different. In those patients with RLU levels indicative of BPH, this would be an expected. In the patient who provided Clinical Sample No. 1, the presence of detectable PSA-specific target RNA in the peripheral blood shortly after surgery indicates that cells expressing PSA mRNA, presumably prostate cancer cells, are still present in peripheral blood, indicative of shed cancer cells or metastasis.

In further testing of clinical samples using the same assay system to detect PSA-specific target RNA in peripheral blood, a total of 30 samples were tested: 5 from normal controls, 15 from patients clinically diagnosed as having prostate cancer and 10 clinically diagnosed with BPH. Each reaction contained about 500 ng of total RNA, and each sample was assayed in triplicate. Samples in which greater than 5,000 mean RLU were detected were scored as positive for prostate cancer, and others were scored as negative for prostate cancer. All of the normal control samples and 9 of the 10 samples from BPH patients were negative. Samples that were positive for PSA-specific target RNA included 11 of the 15 samples from patients clinically diagnosed as having prostate cancer and one of the BPH-diagnosed patients. These results show that the assay for PSA-specific target in peripheral blood was consistent with the clinical symptoms in the majority of cases. For those patients diagnosed with prostate cancer where PSA-specific target was not detected in blood, the cancer may not have metastasized or shed cells into the blood.

EXAMPLE 8

Amplification and Detection of PSA-Specific Target in Various Biological Samples Although prostate specific antigen (PSA) has been associated with cancer in prostate tissue, amplification and detection assays were performed on RNA isolated from other human tissues to determine the relative levels of PSA-specific target detected in those tissues. Unless otherwise indicated, all tissues were obtained from normal donors (i.e., non-cancerous tissue). The assays were performed in triplicate for each sample using either total RNA or poly-A RNA isolated from human tissue samples substantially as described in previous examples using a non-T7(+) primer an oligonucleotide having SEQ ID NO:18, a T7(−) promoter-primer an oligonucleotide having SEQ ID NO:30 and an AE-labeled probe have the oligonucleotide sequence of SEQ ID NO:1. The results of these assays are presented in Table 9, with the negative control results being the mean of 12 reactions performed without adding target RNA.

TABLE 9

Detection of PSA-specific Target in Biological Samples

| Biological Sample | Amount Tested Per Reaction | Mean RLU |
|---|---|---|
| Prostate Tissue Total RNA | 100 ng | 1,695,965 |
| Prostate Tissue Total RNA | 10 ng | 1,832,916 |
| Prostate Tissue Total RNA | 1 ng | 1,170,802 |
| Peripheral Blood Total RNA | 100 ng | 2,341 |
| Breast Tissue Total RNA | 100 ng | 54,787 |
| Breast Tissue Total RNA | 10 ng | 5,486 |
| Lung Tissue Total RNA | 100 ng | 2,319 |
| Negative Control for Total RNA | 0 | 1,620 |
| Prostate Tissue Poly-A RNA | 10 ng | 2,510,601 |

TABLE 9-continued

Detection of PSA-specific Target in Biological Samples

| Biological Sample | Amount Tested Per Reaction | Mean RLU |
|---|---|---|
| Peripheral Blood Poly-A RNA | 10 ng | 1,811 |
| Breast Tissue Poly-A RNA | 10 ng | 120,264 |
| Kidney Tissue Poly-A RNA | 10 ng | 147,284 |
| Liver Tissue Poly-A RNA | 10 ng | 1,900 |
| Negative Control for Poly-A RNA | 0 | 1,586 |
| PSA In vitro Transcripts | 10,000 copies | 1,309,171 |
| PSA In vitro Transcripts | 1,000 copies | 218,205 |
| PSA In vitro Transcripts | 100 copies | 21,421 |
| PSA In vitro Transcripts | 10 copies | 3,771 |

In separate experiments, poly-A RNA isolated from human prostate tissue, peripheral blood, breast tissue, kidney tissue, liver tissue, small intestine and lymph node were compared in similar amplification and detection assays, using the same combination of primers and probe as above. The mRNA for prostate tissue was assayed at 5 fg or 0.5 fg per reaction, and the mRNA from the other biological sources was assayed at 5 ng and 0.5 ng per reaction. Under these conditions, PSA-specific target sequences were detected in the prostate tissue, breast tissue, kidney tissue, small intestine and lymph node, but no signal above the negative control (i.e., reactions without added RNA) was detected in liver tissue or blood. The relative signal (mean RLU of duplicate assays) detected indicated that the PSA target nucleic acid present in breast tissue, kidney tissue, small intestine and lymph node was about $10^5$-fold to $10^6$-fold less than present in prostate tissue.

These results show that the PSA target detection system can detect even relatively small amounts of target in tissues other than prostate tissue. Because some tested tissues (liver and peripheral blood) were negative for PSA-specific target in these assays indicates that the PSA gene is not merely expressed at a lower level in all human tissues besides prostate. Therefore, the PSA target may be a general marker for cancerous or pre-cancerous conditions in selected other human tissues. An increase in detectable PSA-specific target (e.g., in peripheral blood) may then be an indication of metastasized prostate cancer or other types of cancer.

EXAMPLE 9

Amplification and Detection of PSA, PSMA and hK2 Targets in Various Biological Samples In addition to PSA, the other prostate-associated cancer marker targets PSMA and hK2 are also useful for detecting the presence of these target mRNA in non-prostate tissue. Here, amplification and detection assays were performed on total and poly(A) RNA isolated from human tissues to determine the relative levels of PSA, PSMA and hK2 specific target in those tissues. All tissues were obtained from normal donors (i.e., non-cancerous tissue) and the assays were performed in triplicate for each sample, substantially as described in Example 8. For each tested sample, the known amount of RNA or poly(A) RNA was as indicated in Table 10, where 5 ng of poly(A) RNA is equivalent to about 100 ng of total RNA. For PSA detection, transcription-mediated amplification was performed using a non-T7(+) primer having SEQ ID NO:18, a T7(−) promoter-primer having SEQ ID NO:30 and an AE-labeled probe having SEQ ID NO:1. For PSMA detection, transcription-mediated amplification was performed using a non-T7(+) primer having SEQ ID NO:48, a T7(−) promoter-primer having SEQ ID NO:49 and an AE-labeled probe having SEQ ID NO:50. For hK2 detection, transcription-mediated amplification was performed using a non-T7(+) primer having SEQ ID NO:46, a T7(−) promoter-primer having SEQ ID NO:47 and an AE-labeled probe having SEQ ID NO:1. Detection of RLU was substantially as described above. The mean RLU results of the assays performed on triplicate samples for each result are shown in Table 10 (ND means "not done").

TABLE 10

Detection of Prostate-Associated Genetic Marker Targets in Biological Samples

| Tissue/RNA type | RNA Amount | PSA | hK2 | PSMA |
|---|---|---|---|---|
| Prostate | 1 ng | $2.58 \times 10^6$ | $1.37 \times 10^6$ | $1.19 \times 10^6$ |
| Total RNA | 100 pg | $2.54 \times 10^6$ | $3.81 \times 10^5$ | $7.71 \times 10^4$ |
|  | 10 pg | $2.40 \times 10^6$ | $1.54 \times 10^4$ | $8.97 \times 10^3$ |
|  | 1 pg | $2.18 \times 10^6$ | $2.15 \times 10^3$ | $2.08 \times 10^3$ |
|  | 100 fg | $1.87 \times 10^6$ | $1.59 \times 10^3$ | $1.76 \times 10^3$ |
|  | 10 fg | $6.22 \times 10^5$ | ND | ND |
|  | 1 fg | $1.68 \times 10^3$ | ND | ND |
| Blood | 100 ng | $2.12 \times 10^3$ | $1.39 \times 10^3$ | $1.57 \times 10^3$ |
| Total RNA | 10 ng | $1.71 \times 10^3$ | $1.27 \times 10^3$ | $1.51 \times 10^3$ |
| Breast | 100 ng | $2.78 \times 10^6$ | $1.18 \times 10^4$ | $2.04 \times 10^6$ |
| Total RNA | 10 ng | $1.56 \times 10^6$ | $3.14 \times 10^3$ | $1.13 \times 10^6$ |
|  | 1 ng | $1.17 \times 10^6$ | ND | $2.57 \times 10^4$ |
|  | 0.1 ng | $1.84 \times 10^3$ | ND | $4.46 \times 10^3$ |
| Lung | 100 ng | $1.94 \times 10^6$ | $1.29 \times 10^3$ | $1.85 \times 10^6$ |
| Total RNA | 10 ng | $4.27 \times 10^3$ | $1.37 \times 10^3$ | $3.16 \times 10^5$ |
|  | 1 ng | $1.76 \times 10^3$ | ND | $7.20 \times 10^3$ |
|  | 0.1 ng | ND | ND | $2.61 \times 10^3$ |
| Lymph Node | 5 ng | $2.73 \times 10^6$ | $1.59 \times 10^5$ | $2.14 \times 10^6$ |
| Poly(A) RNA | 500 pg | $2.52 \times 10^6$ | $1.68 \times 10^4$ | $1.92 \times 10^5$ |
|  | 50 pg | $7.89 \times 10^5$ | $2.05 \times 10^3$ | $6.84 \times 10^3$ |
|  | 5 pg | $1.66 \times 10^3$ | $1.33 \times 10^3$ | $3.22 \times 10^3$ |
| Kidney | 5 ng | $2.60 \times 10^6$ | $1.24 \times 10^3$ | $2.54 \times 10^6$ |
| Poly(A) RNA | 500 pg | $1.04 \times 10^6$ | $1.29 \times 10^3$ | $8.01 \times 10^5$ |
|  | 50 pg | $1.29 \times 10^5$ | ND | $7.37 \times 10^4$ |
|  | 5 pg | $1.66 \times 10^3$ | ND | $4.31 \times 10^3$ |
| Small Intestine | 5 ng | $2.70 \times 10^6$ | $1.42 \times 10^3$ | $1.34 \times 10^6$ |
| Poly(A) RNA | 500 pg | $6.40 \times 10^5$ | $2.28 \times 10^3$ | $1.73 \times 10^6$ |
|  | 50 pg | $4.89 \times 10^4$ | ND | $1.18 \times 10^5$ |
|  | 5 pg | $3.64 \times 10^3$ | ND | $8.32 \times 10^3$ |

The results shown in Table 10 indicate-that the amplification and detection methods used here detected PSA-specific RNA in a prostate sample containing at least 10 fg of total RNA, in a breast sample containing at least 1 ng of total RNA, in a lung sample containing at least 100 ng of total RNA, and in samples containing at least 50 pg poly(A) RNA isolated from lymph node, kidney and small intestine. For hK2, the assays detected this genetic marker RNA in prostate total RNA (at least 10 pg/sample), breast total RNA (at least 100 ng/sample), and lymph node poly(A) RNA (at least 500 pg/sample). For PSMA, the assays detected this genetic marker RNA in prostate total RNA (at least 10 pg/sample), breast total RNA (at least 1 ng/sample), lung (at least 1 ng/sample) and in poly(A) RNA isolated from lymph node (at least 50 pg/sample), kidney (at least 50 pg/sample) and small intestine (at least 5 pg/sample). None of the primer and probe combinations detected the genetic marker (PSA, hK2; PSMA) in RNA isolated from normal blood, and generally hK2 was detected in lower amounts in the other tissues relative to PSA or PSMA. Table 10 results also show that assays are relatively quantitative, detecting RLU that are relatively proportional to the amount of target-specific RNA in the sample, up to the saturation point of detection (about $2.5 \times 10^6$ RLU in these experiments). Thus standard titration experiments could be used to quantitatively determine the relative amounts of target RNA in a sample.

EXAMPLE 10

Amplification and Detection of PSA, PSMA and hK2 Targets in Clinical Samples

In this example, clinical samples (peripheral blood drawn from patients having benign prostate hyperplasia (BPH) or prostate carcinoma (CaP), or blood drawn from normal controls) were tested in a blinded study where the person performing the assays did not know the source of the tested sample. Total RNA was isolated from the clinical samples using standard guanidium isothiocyanate extraction methods (Sambrook, J. et al., 1989, *Molecular Cloning, A Laboratory Manual*, $2^{nd}$ ed. (Cold Spring Harbor Laboratory Press, Cold Spring Harbor, N.Y.), pp. 7.37-7.57). For amplification using TMA and detection substantially as described earlier herein, each sample was assayed in duplicate using 500 ng for detection of PSA RNA, 500 ng for detection of hK2 RNA and 100 ng for detection of PSMA. Positive samples were those that produced detectable signal above a cutoff point of greater than 5,000 RLU for PSA detection, greater than 10,000 RLU for hK2 detection, and greater than 1,500 RLU for PSMA detection; negative samples were those that produced signal below the cutoff points for each target. The primers and probes were the same as used in the assays described in Example 9 (for PSA, SEQ ID Nos 18, 30 and 1; for PSMA, SEQ ID NOs 48, 49 and 50; and for hK2, SEQ ID NOs 46, 47 and 1). The results of these assays are shown in Table 11, with the specimens grouped according to the disease state of the person from whom the sample was taken.

TABLE 11

Detection of Prostate-associated Genetic Markers in Clinical Samples

| Specimen No. | Disease State | PSA Target | hK2 Target | PSMA Target |
|---|---|---|---|---|
| 1 | CaP | positive | negative | positive |
| 2 | CaP | positive | negative | negative |
| 3 | CaP | positive | negative | negative |
| 4 | CaP | positive | negative | negative |
| 5 | CaP | positive | positive | negative |
| 6 | CaP | positive | positive | negative |
| 7 | CaP | positive | negative | negative |
| 8 | CaP | positive | positive | positive |
| 9 | CaP | positive | negative | negative |
| 10 | CaP | negative | negative | positive |
| 11 | CaP | positive | positive | negative |
| 12 | CaP | positive | positive | negative |
| 28 | CaP | negative | positive | negative |
| 29 | CaP | negative | positive | negative |
| 30 | CaP | negative | negative | negative |
| 13 | Normal Control | negative | negative | negative |
| 14 | Normal Control | negative | negative | negative |
| 15 | Normal Control | negative | negative | negative |
| 16 | Normal Control | negative | negative | positive |
| 17 | Normal Control | negative | positive | negative |
| 18 | BPH | negative | negative | negative |
| 19 | BPH | negative | negative | negative |
| 20 | BPH | positive | positive | negative |
| 21 | BPH | negative | negative | negative |
| 21 | BPH | negative | negative | negative |
| 23 | BPH | negative | negative | positive |
| 24 | BPH | negative | positive | negative |
| 25 | BPH | negative | negative | positive |
| 26 | BPH | negative | positive | negative |
| 27 | BPH | negative | negative | negative |

The results of Table 11 show a generally positive correlation between the clinical status of the sample donor and the detection of PSA. Eleven of fourteen prostate cancer patients were positive, only one of ten BPH patients was positive and none of the normal controls was positive in the assay. Detection of hK2 also showed a positive correlation to prostate carcinoma status (7 of 14 were positive), although one normal control was positive and three BPH patients of ten were positive. Detection of PSMA showed no strong correlation with the clinical status of the donor, but for two of the three prostate cancer patients that tested positive for PSMA, they were also positive for PSA. One prostate cancer patient (specimen 10) was positive only for PSMA and two prostate cancer patients were positive only for hK2. These results show that the assays specifically detect the individual cancer genetic markers in RNA isolated from clinical samples and that each marker individually, or in combination with one or two other prostate-associated genetic cancer marker, is useful for detecting a molecular marker that correlates with prostate cancer. For patients that show symptoms of prostate cancer but test negative with one genetic marker (e.g., PSA), another marker (e.g., hK2) may result in a positive signal, thus decreasing the potential of a false negative diagnosis that would result from reliance on results of only one marker. For prostate cancer patients that test positive for one prostate-associated genetic marker (e.g., PSA), a positive result obtain for another genetic marker (e.g., PSMA or hK2) may be used to further add support to the positive diagnosis or to provide an indication of the extent of tumor growth. In all cases, because the positive results were obtained with non-prostate samples, the results may support the diagnosis that metastasis has occurred.

The examples presented herein are meant to more fully describe preferred embodiments of the present invention which is defined by the claims that follow. All embodiments that are legal equivalents of the invention are anticipated to be within the scope of the claims.

We claim:

1. An oligonucleotide comprising:
    a sequence consisting of a target-binding sequence of SEQ ID NO:41 (AGGCTGTGCCGACCCAGCAAGAT) or its equivalent RNA, or a fully complementary sequence of the target-binding sequence of SEQ ID NO:41 or its equivalent RNA, and
    an optional promoter sequence adjacent to the target-binding sequence.

2. An isolated oligonucleotide consisting essentially of the sequence of any one of SEQ ID NO:14, SEQ ID NO:21, SEQ ID NO:41, or a fully complementary base sequence or equivalent RNA of any of these sequences.

3. An olgonucleotide according to claim 2, consisting essentially of a target-binding sequence of SEQ ID NO:41 (AGGCTGTGCCGACCCAGCAAGAT) without a promoter sequence located 5'of the target-binding sequence.

4. A combination of oligonucleotides used in a detection assay specific for a prostate specific antigen (PSA) target nucleic acid sequence, comprising:
    a first oligonucleotide that includes a sequence consisting essentially of a target-binding sequence of SEQ ID NO:41 (AGGCTGTGCCGACCCAGCAAGAT) or its equivalent RNA, or a fully complementary base sequence of the target-binding sequence of SEQ ID NO:41 or its equivalent RNA, and serves as a first amplification primer that hybridizes specifically to a first PSA-specific sequence contained in exon 3 of a PSA expressed gene sequence;
    a second oligonucleotide consisting essentially of SEQ ID NO:21, or a fully complementary base sequence or equivalent RNA thereof, that serves as a second amplification primer that hybridizes specifically to a different, non-overlapping second PSA-specific sequence contained in axon 2 of a PSA expressed gene sequence; and
    a third oligonucleotide that serves as a detection probe that hybridizes specifically to a third PSA-specific sequence contained in one or more axons of a PSA expressed gene sequence, wherein the third PSA-specific sequence is located between the first and second PSA-specific sequences.

5. The combination at oligonucleotides of claim 4, wherein the third oligonucleotide hybridizes specifically to a third PSA-specific sequence contained in exon 2 of a PSA expressed gene sequence.

6. The combination of oligonucleotides of claim 4, wherein the third oligonucleotide consists essentially of SEQ ID NO:14 or equivalent RNA, or a fully complementary base sequence of SEQ ID NO:14 or its equivalent RNA.

7. The combination of olgonucleotides of claim 4, wherein the combination further includes at least one helper olgonucleotide.

8. The combination of oligonucleotides of claim 7, wherein one helper oligonucleotide consists essentially of SEQ ID NO:27 or its equivalent RNA, or a fully complementary base sequence of SEQ ID NO:27 or its equivalent RNA.

9. The combination of oligonucleotides of claim 7, wherein one helper oligonucleotide consists essentially of SEQ ID NO:28 or its equivalent RNA, or a fully complementary base sequence of SEQ ID NO:28 or its equivalent RNA.

10. A method of detecting a prostate-associated target nucleic acid in a biological sample containing nucleic acid, comprising the steps of:
    providing a nucleic acid sample containing a target nucleic acid that includes at least a portion of at least one expressed gene sequence encoding prostate-specific antigen (PSA), prostate-specific membrane antigen (PSMA) or human kallikrein 2 (hK2);
    hybridizing to the target nucleic acid a first oligonucleotide that includes a sequence consisting essentially of a target-binding sequence of SEQ ID NO:41 (AGGCTGTGCCGACCCAGCAAGAT) or its equivalent RNA or a fully complementary base sequence of the target-binding sequence of SEQ ID NO:41 or its equivalent RNA and an optional promoter sequence adjacent to the target-binding sequence, that serves as a first amplification prime;
    hybridizing to the target nucleic acid or a complementary strand of the target nucleic acid a second oligonucleotide consisting essentially of SEQ ID NO:21 or its equivalent RNA, or a fully complementary base sequence of SEQ ID NO:21 or its equivalent RNA, that serves as a second amplification primer;

producing a plurality of amplification products of the target nucleic acid by using the first and second amplification primers and at least one polymerase activity;

providing a probe oligonucleotide that hybridizes specifically to at least one amplification product of the target nucleic acid; and detecting a signal resulting from the probe hybridized to the amplification product.

11. The method of claim 10, wherein the probe oligonucleotide hybridizes specifically to a sequence of exon 2 of the gene sequence encoding PSA.

12. The method of claim 10, wherein the probe oligonucleotide consists essentially of SEQ ID NO:14.

13. The method of claim 10, further comprising including at least one helper oligonucleotide of SEQ ID NO:27 or SEQ ID NO:28.

14. The method of claim 10, wherein a nucleic acid specific for the prostate-specific membrane antigen (PSMA) is also detected.

15. The method of claim 14, wherein the nucleic acid specific for PSMA is detected by using a combination of oligonucleotides of SEQ ID NO:48, SEQ ID NO:49, and SEQ ID NO:50.

16. The method of claim 10, wherein a nucleic acid specific for the human kallikrein 2 (hK2) is also detected.

17. The method of claim 16, wherein the nucleic acid specific for hK2 is detected by using a combination of oligonucleotides of SEQ ID NO:46, SEQ ID NO:47, and SEQ ID NO:1.

* * * * *

UNITED STATES PATENT AND TRADEMARK OFFICE
CERTIFICATE OF CORRECTION

PATENT NO.       : 7,267,956 B2  
APPLICATION NO.  : 10/978145  
DATED            : September 11, 2007  
INVENTOR(S)      : Harvey et al.

It is certified that error appears in the above-identified patent and that said Letters Patent is hereby corrected as shown below:

In claim 3, at column 53, line 40, delete "5'of" and insert in its place -- 5' of --.

In claim 4, at column 53, line 64, delete "axons" and insert in its place -- exons --.

In claim 10, at column 54, lie 61, delete "prime" and insert in its place -- primer --.

Signed and Sealed this

Twentieth Day of November, 2007

JON W. DUDAS  
*Director of the United States Patent and Trademark Office*

SEQUENCE LISTING

```
<160> NUMBER OF SEQ ID NOS: 50

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: synthetic
      construct

<400> SEQUENCE: 1
ggaccacctg ctacgcctca g                                                 21

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: synthetic
      construct

<400> SEQUENCE: 2
gaccaagttc atgctgtgtg ctg                                               23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: synthetic
      construct

<400> SEQUENCE: 3
gaccaagttc atgctgtgtg ctg                                               23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: synthetic
      construct

<400> SEQUENCE: 4
gctgtgaagg tcatggacct gcc                                               23
```

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: synthetic
      construct

<400> SEQUENCE: 5
gaaccagagg agttcttgac cc                                              22

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: synthetic
      construct

<400> SEQUENCE: 6
ggccagatgg tgcagccggg agc                                             23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: synthetic
      construct

<400> SEQUENCE: 7
gcagtctgcg gcggtgttct g                                               21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: synthetic
      construct

<400> SEQUENCE: 8
acagctgccc actgcatcag g                                               21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: synthetic
      construct

<400> SEQUENCE: 9
gttcaccctc agaaggtgac c                                               21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: synthetic
      construct

<400> SEQUENCE: 10
gctgtgtgct ggacgctgga c                                               21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: synthetic
      construct

<400> SEQUENCE: 11
gcttgtggcc tctcgtggca g                                              21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: synthetic
      construct

<400> SEQUENCE: 12
tggcctctcg tggcagggca gt                                             22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: synthetic
      construct

<400> SEQUENCE: 13
tctcgtggca gggcagtctg c                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: synthetic
      construct

<400> SEQUENCE: 14 gtgcacccccc agtgggtcct c                                             21

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: synthetic
      construct

<400> SEQUENCE: 15
gatgctgtga aggtcatgga cctg                                           24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: synthetic
      construct

<400> SEQUENCE: 16
gtgcgcaagt tcaccctcag aagg                                           24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: synthetic
      construct

<400> SEQUENCE: 17
gaaggtcatg gacctgccca ccca                                          24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: synthetic
      construct

<400> SEQUENCE: 18
ctgtcagagc ctgccgagct cacg                                          24

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: synthetic
      construct

<400> SEQUENCE: 19
gctgctccgc ctgtcagagc ctg                                           23

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: synthetic
      construct

<400> SEQUENCE: 20
gcttgtggcc tctcgtggca g                                             21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: synthetic
      construct

<400> SEQUENCE: 21
tctcgtggca gggcagtctg c                                             21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: synthetic
      construct

<400> SEQUENCE: 22
ttccaatgac gtgtgtgcgc a                                             21

<210> SEQ ID NO 23

```
<211> LENGTH: 24
<212> TYPE: DNA
<213> ORGANISM: Artificial Sequence
<220> FEATURE:
<223> OTHER INFORMATION: Description of Artificial Sequence: synthetic
      construct

<400> SEQUENCE: 23
ggaggctggg agtgcgagaa gcat                                              24

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: synthetic
      construct

<400> SEQUENCE: 24
ggctgggagt gcgagaagca tt                                                22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: synthetic
      construct

<400> SEQUENCE: 25
tggcctctcg tggcagggca gt                                                22

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: synthetic
      construct

<400> SEQUENCE: 26
gcagtctgcg gcggtgttct g                                                 21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: synthetic
      construct

<400> SEQUENCE: 27 gtgcacccccc agtgggtcct c                                                21

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: synthetic
      construct

<400> SEQUENCE: 28
aacaaaagcg tgatcttgct ggg                                               23

<210> SEQ ID NO 29
<211> LENGTH: 22
```

```
<212> TYPE: DNA
<213> ORGANISM: Artificial Sequence
<220> FEATURE:
<223> OTHER INFORMATION: Description of Artificial Sequence: synthetic
      construct

<400> SEQUENCE: 29
caaaagcgtg atcttgctgg gt                                              22

<210> SEQ ID NO 30
<211> LENGTH: 54
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: promoter
<222> LOCATION: (1)..(28)

<400> SEQUENCE: 30
taaattaata cgactcacta tagggagacc agagggtgaa cttgcgcaca cacg           54

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: promoter
<222> LOCATION: (1)..(28)

<400> SEQUENCE: 31
taaattaata cgactcacta tagggagact gcaccacctt ggtgtacagg                50

<210> SEQ ID NO 32
<211> LENGTH: 54
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: promoter
<222> LOCATION: (1)..(28)

<400> SEQUENCE: 32
taaattaata cgactcacta tagggagact catggttcac tgccccatga cgtg           54

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: promoter
<222> LOCATION: (1)..(27)

<400> SEQUENCE: 33
aatttaatac gactcactat agggagatgc accaccttgg tgtacagg                  48

<210> SEQ ID NO 34
<211> LENGTH: 51
<212> TYPE: DNA
<213> ORGANISM: Artificial Sequence
```

```
<220> FEATURE:
<223> OTHER INFORMATION: Description of Artificial Sequence: synthetic
      construct
<220> FEATURE:
<221> NAME/KEY: promoter
<222> LOCATION: (1)..(27)

<400> SEQUENCE: 34
aatttaatac gactcactat agggagacat ggttcactgc cccatgacgt g      51

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: promoter
<222> LOCATION: (1)..(27)

<400> SEQUENCE: 35
aatttaatac gactcactat agggagagag ggtgaacttg cgcacacacg          50

<210> SEQ ID NO 36
<211> LENGTH: 52
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: promoter
<222> LOCATION: (1)..(28)

<400> SEQUENCE: 36
taaattaata cgactcacta tagggagacc accttctgag ggtgaacttg cg      52

<210> SEQ ID NO 37
<211> LENGTH: 49
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: promoter
<222> LOCATION: (1)..(28)

<400> SEQUENCE: 37
taaattaata cgactcacta tagggagagc cgacccagca agatcacgc            49

<210> SEQ ID NO 38
<211> LENGTH: 49
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: promoter
<222> LOCATION: (1)..(28)

<400> SEQUENCE: 38
taaattaata cgactcacta tagggagact gtggctgacc tgaaatacc            49

<210> SEQ ID NO 39
<211> LENGTH: 49
<212> TYPE: DNA
```

<213> ORGANISM: Artificial Sequence
<220> FEATURE:
<223> OTHER INFORMATION: Description of Artificial Sequence: synthetic construct
<220> FEATURE:
<221> NAME/KEY: promoter
<222> LOCATION: (1)..(28)

<400> SEQUENCE: 39
taaattaata cgactcacta tagggagagt gtacagggaa ggcctttcg                49

<210> SEQ ID NO 40
<211> LENGTH: 50
<212> TYPE: DNA
<213> ORGANISM: Artificial Sequence
<220> FEATURE:
<223> OTHER INFORMATION: Description of Artificial Sequence: synthetic construct
<220> FEATURE:
<221> NAME/KEY: promoter
<222> LOCATION: (1)..(28)

<400> SEQUENCE: 40
taaattaata cgactcacta tagggagaac ccagcaagat cacgcttttg               50

<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: synthetic construct
<220> FEATURE:
<221> NAME/KEY: promoter
<222> LOCATION: (1)..(28)

<400> SEQUENCE: 41
taaattaata cgactcacta tagggagaag gctgtgccga cccagcaaga t             51

<210> SEQ ID NO 42
<211> LENGTH: 52
<212> TYPE: DNA
<213> ORGANISM: Artificial Sequence
<220> FEATURE:
<223> OTHER INFORMATION: Description of Artificial Sequence: synthetic construct
<220> FEATURE:
<221> NAME/KEY: promoter
<222> LOCATION: (1)..(28)

<400> SEQUENCE: 42
taaattaata cgactcacta tagggagacc tgtgtcttca ggatgaaaca gg            52

<210> SEQ ID NO 43
<211> LENGTH: 52
<212> TYPE: DNA
<213> ORGANISM: Artificial Sequence
<220> FEATURE:
<223> OTHER INFORMATION: Description of Artificial Sequence: synthetic construct
<220> FEATURE:
<221> NAME/KEY: promoter
<222> LOCATION: (1)..(28)

<400> SEQUENCE: 43
taaattaata cgactcacta tagggagact gacctgaaat acctggcctg tg            52

<210> SEQ ID NO 44
<211> LENGTH: 28

```
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: promoter
<222> LOCATION: (1)..(28)

<400> SEQUENCE: 44
taaattaata cgactcacta tagggaga                                            28

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: promoter
<222> LOCATION: (1)..(27)

<400> SEQUENCE: 45
aatttaatac gactcactat agggaga                                             27

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: synthetic
      construct

<400> SEQUENCE: 46
gtcagagcct gccaagatca cag                                                 23

<210> SEQ ID NO 47
<211> LENGTH: 55
<212> TYPE: DNA
<213> ORGANISM: Artificial Sequence
<220> FEATURE:
<223> OTHER INFORMATION: Description of Artificial Sequence: synthetic
      construct
<220> FEATURE:
<221> NAME/KEY: promoter
<222> LOCATION: (1)..(28)

<400> SEQUENCE: 47
taaattaata cgactcacta tagggagacc accagcacac aacatgaact ctgtc              55

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: synthetic
      construct

<400> SEQUENCE: 48
cagatatgtc attctgggag gtc                                                 23

<210> SEQ ID NO 49
<211> LENGTH: 54
<212> TYPE: DNA
<213> ORGANISM: Artificial Sequence
<220> FEATURE:
<223> OTHER INFORMATION: Description of Artificial Sequence: synthetic
      construct
```

-continued

```
<220> FEATURE:
<221> NAME/KEY: promoter
<222> LOCATION: (1)..(28)

<400> SEQUENCE: 49
taaattaata cgactcacta tagggagacc aaattcttct gcatcccagc ttgc        54

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: synthetic
      construct

<400> SEQUENCE: 50
ctcagagtgg agcagctgtt gttc                                        24
```